(12) United States Patent
Toth et al.

(10) Patent No.: US 12,131,413 B2
(45) Date of Patent: Oct. 29, 2024

(54) VISUALIZING PHYSIOLOGIC DATA OBTAINED FROM SUBJECTS

(71) Applicant: LifeLens Technologies, LLC, Ivyland, PA (US)

(72) Inventors: Landy Toth, Doylestown, PA (US); Dhananjai Hariharan, Doylestown, PA (US); Robert S. Schwartz, Inver Grove Heights, MN (US)

(73) Assignee: LifeLens Technologies, LLC, Ivyland, PA (US)

( * ) Notice: Subject to any disclaimer, the term of this patent is extended or adjusted under 35 U.S.C. 154(b) by 61 days.

(21) Appl. No.: 17/920,491

(22) PCT Filed: Apr. 22, 2021

(86) PCT No.: PCT/US2021/028611
§ 371 (c)(1),
(2) Date: Oct. 21, 2022

(87) PCT Pub. No.: WO2021/216847
PCT Pub. Date: Oct. 28, 2021

(65) Prior Publication Data
US 2023/0147888 A1 May 11, 2023

Related U.S. Application Data

(60) Provisional application No. 63/014,757, filed on Apr. 24, 2020.

(51) Int. Cl.
*G06T 11/20* (2006.01)
*A61B 5/00* (2006.01)
(Continued)

(52) U.S. Cl.
CPC .......... *G06T 11/206* (2013.01); *A61B 5/0006* (2013.01); *A61B 5/339* (2021.01);
(Continued)

(58) Field of Classification Search
None
See application file for complete search history.

(56) References Cited

U.S. PATENT DOCUMENTS

2009/0299201 A1  12/2009  Gunderson
2012/0323133 A1  12/2012  Lindauer et al.
(Continued)

FOREIGN PATENT DOCUMENTS

EP  0621540  10/1994
WO  0014687  3/2000
(Continued)

OTHER PUBLICATIONS

International Search Report and Written Opinion of PCT/US2021/028611 dated Aug. 3, 2021, 10 pages.
(Continued)

*Primary Examiner* — Jwalant Amin
(74) *Attorney, Agent, or Firm* — Ryan, Mason & Lewis, LLP

(57) ABSTRACT

An apparatus comprises at least one processing device comprising a processor coupled to a memory. The at least one processing device is configured to select physiologic data to be visualized, the selected physiologic data comprising a given set of one or more physiologic parameters collected from a given set of one or more subjects over a given period of time. The at least one processing device is also configured to determine a plot type for visualization of the selected physiologic data, the plot type being determined based at least in part on a repetitiveness of the selected physiologic data over a plurality of time segments in the given period of time. The at least one processing device is further configured to generate a visualization of the selected physiologic data utilizing the determined plot type, and to
(Continued)

output the generated visualization of the selected physiologic data via an interactive graphical user interface.

20 Claims, 21 Drawing Sheets

(51) Int. Cl.
  *A61B 5/339* (2021.01)
  *A61B 5/384* (2021.01)
  *G16H 20/30* (2018.01)
  *G16H 40/67* (2018.01)
  *G16H 50/50* (2018.01)
(52) U.S. Cl.
  CPC ............ *A61B 5/384* (2021.01); *A61B 5/4812* (2013.01); *A61B 5/7435* (2013.01); *A61B 5/748* (2013.01); *G16H 20/30* (2018.01); *G16H 40/67* (2018.01); *G16H 50/50* (2018.01); *G06T 2200/24* (2013.01); *G06T 2210/41* (2013.01)

(56) References Cited

U.S. PATENT DOCUMENTS

| | | |
|---|---|---|
| 2015/0335288 A1 | 11/2015 | Toth et al. |
| 2017/0156619 A1 | 6/2017 | Couderc et al. |
| 2018/0296108 A1 | 10/2018 | Stewart et al. |
| 2018/0330805 A1 | 11/2018 | Cheung et al. |

FOREIGN PATENT DOCUMENTS

| | | |
|---|---|---|
| WO | 2014197822 A2 | 12/2014 |
| WO | 2016019250 A1 | 2/2016 |
| WO | 2017190049 A1 | 11/2017 |
| WO | 2018195052 | 10/2018 |
| WO | 2019226506 | 11/2019 |

OTHER PUBLICATIONS

European Patent Application No. 21791927.3-1113, Supplementary European Search Report, May 23, 2024, 11 pages.

FIG. 7

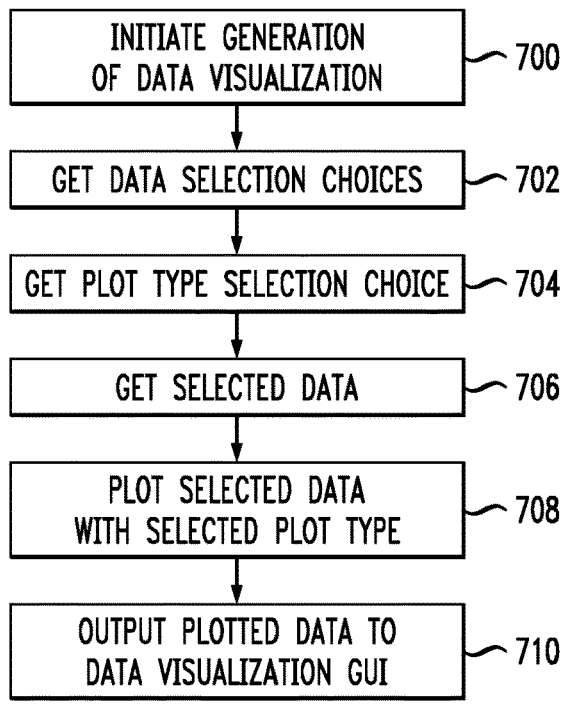

- INITIATE GENERATION OF DATA VISUALIZATION — 700
- GET DATA SELECTION CHOICES — 702
- GET PLOT TYPE SELECTION CHOICE — 704
- GET SELECTED DATA — 706
- PLOT SELECTED DATA WITH SELECTED PLOT TYPE — 708
- OUTPUT PLOTTED DATA TO DATA VISUALIZATION GUI — 710

FIG. 8

| PATIENT IDENTIFIER (ID) | DATE/ TIME | HEART RATE (HR) (bpm) | BLOOD PRESSURE (BP) (mmHg) | OXYGEN SATURATION (SpO2) (%) | RESPIRATORY RATE (bpm) | QRS DURATION (ms) |
|---|---|---|---|---|---|---|
| 3965786 | 11/21/19 11:46:28 | 64 | 120/86 | 97 | 11 | 89 |
| 3965786 | 11/21/19 11:46:30 | 64 | 120/86 | 97 | 11 | 91 |
| 3965786 | 11/21/19 11:46:32 | 64 | 120/86 | 97 | 11 | 90 |
| 3965786 | 11/21/19 11:46:34 | 65 | 120/86 | 97 | 11 | 92 |
| 3965786 | 11/21/19 11:46:36 | 65 | 120/86 | 97 | 11 | 89 |

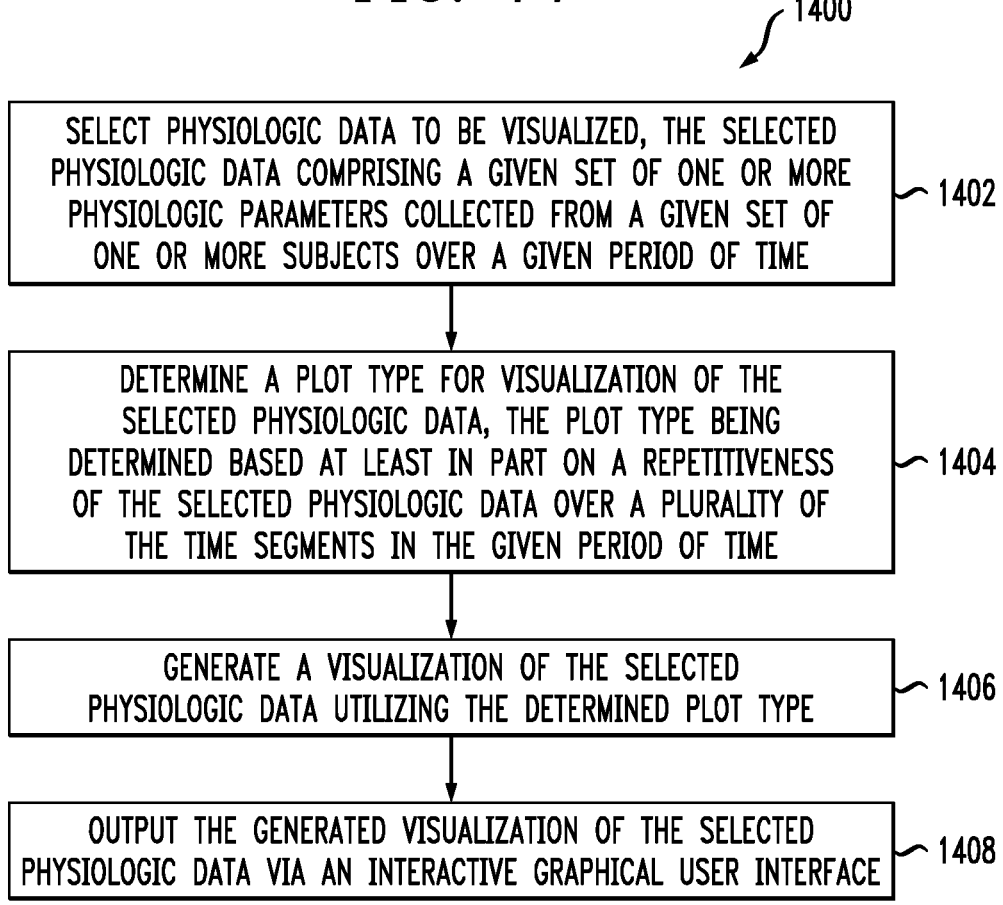

VISUALIZING PHYSIOLOGIC DATA OBTAINED FROM SUBJECTS

TECHNICAL FIELD

The present disclosure relates to the field of physiologic monitoring and, more particularly, to devices and systems for visualizing physiologic data obtained from one or more subjects.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Physiologic monitoring is performed for a range of purposes. Existing technologies, however, are not without shortcomings. For example, there is a need to measure physiologic parameters of subjects reliably, simply, and without cables. As the proliferation of mobile and remote medicine increases, simplified and unobtrusive means for monitoring the physiologic parameters of a patient become more important.

Further, there is a need to quickly convey information to a clinician, nurse, caregiver, or subject that allows for rapid interpretation of a data set. Often, in the context of human life, there are events and behaviors that happen throughout the day that may impact physiology or a disease state. Such events may have a relationship with a time of day, correspond to a particular event performed during the day, a sleep state, etc. Conventional techniques, however, lack the ability to provide or display such data in a format that reflects the cyclical nature thereof.

SUMMARY

One illustrative, non-limiting objective of this disclosure is to provide systems, devices, methods, and kits for visualizing selected physiologic data collected from one or more subjects.

The above illustrative, non-limiting objectives are wholly or partially met by devices, systems, and methods according to the appended claims in accordance with the present disclosure. Features and aspects are set forth in the appended claims, in the following description, and in the annexed drawings in accordance with the present disclosure.

In some embodiments, an apparatus comprises at least one processing device comprising a processor coupled to a memory. The at least one processing device is configured to select physiologic data to be visualized, the selected physiologic data comprising a given set of one or more physiologic parameters collected from a given set of one or more subjects over a given period of time. The at least one processing device is also configured to determine a plot type for visualization of the selected physiologic data, the plot type being determined based at least in part on a repetitiveness of the selected physiologic data over a plurality of time segments in the given period of time. The at least one processing device is further configured to generate a visualization of the selected physiologic data utilizing the determined plot type, and to output the generated visualization of the selected physiologic data via an interactive graphical user interface.

Selecting the physiologic data to be visualized may comprise selecting the given set of one or more subjects, the given set of one or more physiologic parameters, and the given period of time from a database of available physiologic data. The database of available physiologic data may comprise a plurality of entries, each entry being associated with a given subject identifier for a given one of a plurality of subjects, a given timestamp, and a plurality of physiologic parameters collected from the given subject at the given timestamp. Selecting the physiologic data to be visualized from the database of available physiologic data may comprise obtaining the given set of one or more physiologic parameters from a selected subset of entries from the database of available physiologic data, the selected subset of entries having subject identifiers for the given set of one or more subjects and timestamps within the given period of time.

Determining the plot type for visualization of the selected physiologic data may comprise dividing the given period of time into a plurality of time segments, comparing data in at least a subset of a plurality of possible pairs of the plurality of time segments for repetitiveness, and, responsive to determining that the data in at least a threshold number of the plurality of possible pairs of the plurality of time segments are repetitive with respect to one another, selecting a polar coordinate plot type for visualizing the selected physiologic data. Responsive to determining that the data in at least the threshold number of the plurality of possible pairs of the plurality of time segments are not repetitive with respect to one another, a Cartesian coordinate plot type may be selected for visualizing the selected physiologic data. The threshold number of the plurality of possible pairs of the plurality of time segments may comprise a designated percentage of a total number of the plurality of possible pairs of the plurality of time segments.

Determining the plot type for visualization of the selected physiologic data may further comprise identifying a set of supported time segment sizes, and performing one or more iterations of (i) dividing the given period of time into the plurality of time segments utilizing a given one of the set of supported time segment sizes and (ii) comparing the data in at least the subset of the plurality of possible pairs of the plurality of time segments of the given supported time segment size until a determination is made that the data in at least the threshold number of the plurality of possible pairs of the plurality of time segments of the given supported time segment size are repetitive with respect to one another. A first one of the one or more iterations may utilize a smallest one of the set of supported time segment sizes and one or more subsequent ones of the one or more iterations may utilize next largest ones of the set of supported time segment sizes. The smallest one of the set of supported time segment sizes may comprise one day. Responsive to determining that the data in at least the threshold number of the plurality of possible pairs of the plurality of time segments are not repetitive with respect to one another in at least a threshold number of the one or more iterations, a Cartesian coordinate plot type may be selected for visualizing the selected physiologic data.

Selecting the physiologic data to be visualized may further comprise identifying one or more annotations associated with one or more designated time ranges within the given period of time, and outputting the generated visualization of the selected physiologic data via the interactive graphical user interface may comprise displaying one or more user-activable interface features for the one or more annotations at respective points along a circumference of the polar coordinate plot corresponding to the one or more designated time ranges within the given period of time. At least a given one of the one or more annotations may comprise one or more contextual events associated with the given subject at a given one of the one or more designated time ranges. At least a given one of the one or more contextual events comprises at least one of: administering a medication to the given subject; a change in posture or position of the given subject; an indication of pain or discomfort of the given subject; an indication of a sleep state of the given subject; and an indication of a physical activity level of the given subject. The given annotation may comprise a voice recording captured by a given one of the subjects or a caregiver of the given subject, the voice recording describing at least a given one of the one or more contextual events.

Outputting the generated visualization of the selected physiologic data via the interactive graphical user interface may comprise providing one or more user-activatable interface features for overlaying one or more filters on the polar coordinate plot. Each of the plurality of time segments may comprise one day, and at least a given one of the one or more filters may comprise at least one of overlaying visual indicators of daytime and nighttime on the polar coordinate plot and overlaying visual indicators of a sleep state of a given one of the one or more subjects on the polar coordinate plot. At least a given one of the one or more filters may comprise displaying a threshold value of a given one of the one or more physiologic parameters as a ring on the polar coordinate plot.

Outputting the generated visualization of the selected physiologic data via the interactive graphical user interface may comprise providing one or more user-activatable interface features for at least one of toggling a display of individual ones of the set of one or more physiologic parameters on the polar coordinate plot and selecting a given region of the polar coordinate plot corresponding to a given time range within the given period of time. Responsive to selecting the given region of the polar coordinate plot, the interactive graphical user interface may at least one of update the polar coordinate plot to zoom in to the given time range corresponding to the selected given region of the polar coordinate plot and present an additional polar coordinate plot that is zoomed in to the given time range corresponding to the selected given region of the polar coordinate plot. Outputting the generated visualization of the selected physiologic data may further comprise outputting a linear time trace of at least a given one of the set of one or more physiologic parameters, and responsive to selecting the given region of the given polar coordinate plot the interactive graphical user interface may zoom the linear time trace to the given time range corresponding to the selected given region of the polar coordinate plot.

In some embodiments, a computer program product comprises a non-transitory processor-readable storage medium having stored therein executable program code. The executable program code, when executed, causes at least one processing device to select physiologic data to be visualized, the selected physiologic data comprising a given set of one or more physiologic parameters collected from a given set of one or more subjects over a given period of time. The executable program code, when executed, also causes the at least one processing device to determine a plot type for visualization of the selected physiologic data, the plot type being determined based at least in part on a repetitiveness of the selected physiologic data over a plurality of time segments in the given period of time. The executable program code, when executed, further causes the at least one processing device to generate a visualization of the selected physiologic data utilizing the determined plot type, and to output the generated visualization of the selected physiologic data via an interactive graphical user interface.

In some embodiments, a method comprises selecting physiologic data to be visualized, the selected physiologic data comprising a given set of one or more physiologic parameters collected from a given set of one or more subjects over a given period of time. The method also comprises determining a plot type for visualization of the selected physiologic data, the plot type being determined based at least in part on a repetitiveness of the selected physiologic data over a plurality of time segments in the given period of time. The method further comprises generating a visualization of the selected physiologic data utilizing the determined plot type, and outputting the generated visualization of the selected physiologic data via an interactive graphical user interface. The method is performed by at least one processing device comprising a processor coupled to a memory.

BRIEF DESCRIPTION OF THE DRAWINGS

Several aspects of the disclosure can be better understood with reference to the following drawings. In the drawings, like reference numerals designate corresponding parts throughout the several views.

FIG. 7 illustrates a process flow for creating a data visualization with the FIG. 3 data visualization system utilizing the selected data obtained using the FIG. 5 processing flow the data visualization type obtained using the FIG. 6 process flow, according to an embodiment of the invention.

FIG. 8 illustrates physiologic data utilized for creating one or more data visualizations, according to an embodiment of the invention.

FIG. 14 is a flow diagram of an exemplary process for visualizing physiologic data collected from one or more subjects, according to an embodiment of the invention.

DETAILED DESCRIPTION

Figure 1:
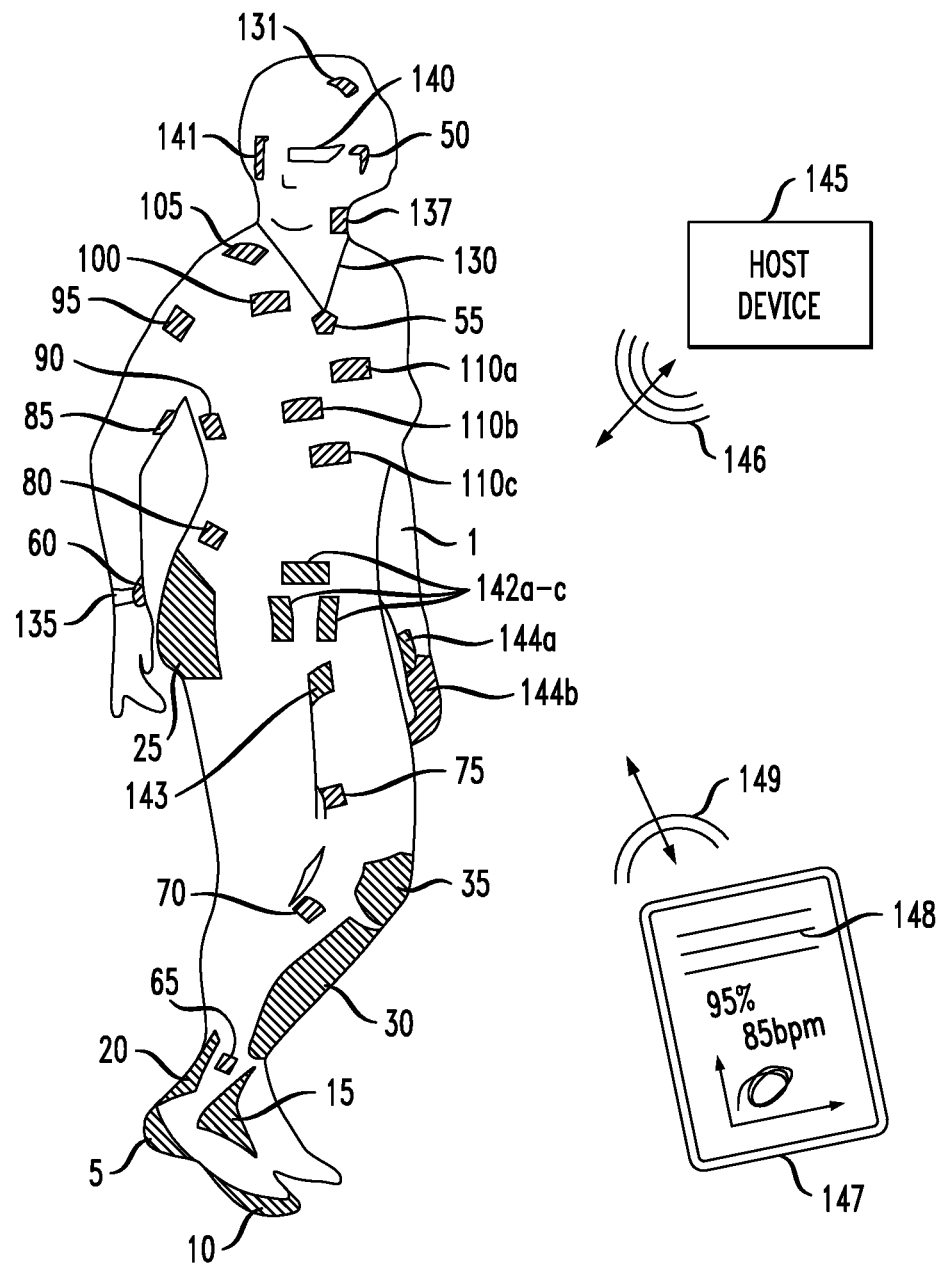
FIG. 1 illustrates aspects of a modular physiologic monitoring system, according to an embodiment of the invention.

Particular embodiments of the present disclosure are described herein below with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

One illustrative, non-limiting objective of this disclosure is to provide systems, devices, methods, and kits for monitoring physiologic and/or physical signals from a subject. Another illustrative, non-limiting objective is to provide simplified systems for monitoring subjects. Another illustrative, non-limiting objective is to provide comfortable long-term wearable systems for monitoring subjects. Yet another illustrative, non-limiting objective is to provide systems for facilitating interaction between a user and a subject with regard to physiologic monitoring of the subject.

The above illustrative, non-limiting objectives are wholly or partially met by devices, systems, and methods according to the appended claims in accordance with the present disclosure. Features and aspects are set forth in the appended claims, in the following description, and in the annexed drawings in accordance with the present disclosure.

A modular physiologic monitoring system in accordance with the present disclosure is configured to monitor one or more physiologic and/or physical signals, also referred to herein as physiologic parameters, of a subject (e.g., a human subject, a patient, an athlete, a trainer, an animal such as equine, canine, porcine, bovine, etc.). The modular physiologic monitoring system may include one or more patches, each patch adapted for attachment to the body of the subject (e.g., attachable to the skin thereof, reversibly attachable, adhesively attachable, with a disposable interface and a reusable module, etc.). In aspects, the physiologic monitoring system may also include one or more modules, configured and dimensioned to mate with corresponding ones of the one or more patches, and to interface with the subject therethrough. One or more of the modules may be configured to convey and/or store one or more physiologic and/or physical signals, signals derived therefrom, and/or metrics derived therefrom obtained via the interface with the subject.

Each module may include a power source (e.g., a battery, a rechargeable battery, an energy harvesting transducer, microcircuit, an energy reservoir, a thermal gradient harvesting transducer, a kinetic energy harvesting transducer, a radio frequency energy harvesting transducer, a fuel cell, a biofuel cell, etc.), signal conditioning circuitry, communication circuitry, one or more sensors, or the like, configured to generate one or more signals (e.g., physiologic and/or physical signals), stimulus, etc.

One or more of the patches may include one or more interconnects, configured and dimensioned so as to couple with one or more of the modules, said modules including a complementary interconnect configured and dimensioned to couple with the corresponding patch. The patch may include a bioadhesive interface for attachment to the subject, the module retainable against the subject via interconnection with the patch.

In aspects, the patch may be configured so as to be single use (e.g., disposable). The patch may include a thin, breathable, stretchable laminate. In aspects, the laminate may include a substrate, a bioadhesive, one or more sensing or stimulating elements in accordance with the present disclosure, and one or more interconnects for coupling one or more of the sensing elements with a corresponding module.

In aspects, to retain a high degree of comfort and long term wearability of the patch on a subject, to limit interference with normal body function, to limit interference with joint movement, or the like, the patch may be sufficiently thin and frail, such that it may not substantially retain a predetermined shape while free standing. Such a definition is described in further detail below. The patch may be provided with a temporary stiffening film to retain the shape thereof prior to placement of the patch onto the body of a subject. Once adhered to the subject, the temporary stiffening film may be removed from the patch. While the patch is adhered to the subject, the shape and functionality of the patch may be substantially retained. Upon removal of the patch from the subject, the now freestanding patch is sufficiently frail such that the patch can no longer substantially retain the predetermined shape (e.g., sufficiently frail such that the patch will not survive in a free standing state). In aspects, stretch applied to the patch while removing the patch from the subject may result in snap back once the patch is in a freestanding state that renders such a patch to crumple into a ball and no longer function.

In aspects, the patch may include a film (e.g., a substrate), with sufficiently high tear strength, such that, as the patch is peeled from the skin of a subject, the patch does not tear. In aspects, the ratio between the tear strength of the patch and the peel adhesion strength of the patch to skin (e.g., tear strength: peel adhesion strength), is greater than 8:1, greater than 4:1, greater than 2:1, or the like. Such a configuration may be advantageous so as to ensure the patch may be easily and reliably removed from the subject after use without tearing.

In aspects, the patch may include a bioadhesive with peel tack to mammalian skin of greater than 0.02 Newtons per millimeter (N/mm), greater than 0.1 N/mm, greater than 0.25 N/mm, greater than 0.50 N/mm, greater than 0.75 N/mm, greater than 2 N/mm, or the like. Such peel tack may be approximately determined using an American Society for Testing and Materials (ASTM) standard test, ASTM D3330: Standard test method for peel adhesion of pressure-sensitive tape.

In aspects, the patch may exhibit a tear strength of greater than 0.5 N/mm, greater than 1 N/mm, greater than 2 N/mm, greater than 8 N/mm, or the like. Such tear strength may be approximately determined using an ASTM standard test, ASTM D624: Standard test method for tear strength of conventional vulcanized rubber and thermoplastic elastomers. In aspects, a patch interface in accordance with the present disclosure may have a ratio between the tear strength of the patch and the peel tack of the adhesive to mammalian skin is greater than 8:1, greater than 4:1, greater than 2:1, or the like.

In aspects, the patch may be provided with a characteristic thickness of less than 50 micrometer (µm), less than 25 µm, less than 12 µm, less than 8 µm, less than 4 µm, or the like. Yet, in aspects, a balance between the thickness, stiffness, and tear strength may be obtained so as to maintain sufficiently high comfort levels for a subject, minimizing skin stresses during use (e.g., minimizing skin stretch related discomfort and extraneous signals as the body moves locally around the patch during use), minimizing impact on skin health, minimizing risk of rucking during use, and minimizing risk of maceration to the skin of a subject, while limiting risk of tearing of the patch during removal from a subject, etc.

In aspects, the properties of the patch may be further altered so as to balance the hydration levels of one or more hydrophilic or amphiphilic components of the patch while attached to a subject. Such adjustment may be advantageous to prevent over hydration or drying of an ionically conducting component of the patch, to manage heat transfer coefficients within one or more elements of the patch, to manage salt retention into a reservoir in accordance with the present disclosure, and/or migration during exercise, to prevent pooling of exudates, sweat, or the like into a fluid measuring sensor incorporated into the patch or associated module, etc. In aspects, the patch or a rate determining component thereof may be configured with a moisture vapor transmission rate of between 200 grams per meter squared per 24 hours ($g/m^2/24$ hrs) and 20,000 $g/m^2/24$ hrs, between 500 $g/m^2/24$ hrs and 12,000 $g/m^2/24$ hrs, between 2,000 $g/m^2/24$ hrs and 8,000 $g/m^2/24$ hrs, or the like.

Such a configuration may be advantageous for providing a comfortable wearable physiologic monitor for a subject, while reducing material waste and/or cost of goods, preventing contamination or disease spread through uncontrolled re-use, and the like.

In aspects, one or more patches and/or modules may be configured for electrically conducting interconnection, inductively coupled interconnection, capacitively coupled interconnection, with each other. In the case of an electrically conducting interconnect, each patch and module interconnect may include complementary electrically conducting connectors, configured and dimensioned so as to mate together upon attachment. In the case of an inductively or capacitively coupled interconnect, the patch and module may include complementary coils or electrodes configured and dimensioned so as to mate together upon attachment.

Each patch or patch-module pair may be configured as a sensing device to monitor one or more local physiologic and/or physical parameters of the attached subject (e.g., local to the site of attachment, etc.), local environment, combinations thereof, or the like, and to relay such information in the form of signals to a host device (e.g., via a wireless connection, via a body area network connection, or the like), one or more patches or modules on the subject, or the like. Each patch and/or patch-module pair may also or alternatively be configured as a stimulating device to apply a stimulus to the subject in response to signaling from the host device, the signaling being based on analysis of the physiologic and/or physical parameters of the subject measured by the sensing device(s).

In aspects, the host device may be configured to coordinate information exchange to/from each module and/or patch, and to generate one or more physiologic signals, physical signals, environmental signals, kinetic signals, diagnostic signals, alerts, reports, recommendation signals, commands, combinations thereof, or the like for the subject, a user, a network, an electronic health record (EHR), a database (e.g., as part of a data management center, an EHR, a social network, etc.), a processor, combinations thereof, or the like. In aspects, the host device may include features for recharging and/or performing diagnostic tests on one or more of the modules. In aspects, a host device in accordance with the present disclosure may be integrated into a bedside alarm clock, housed in an accessory, within a purse, a backpack, a wallet, or may be included in a mobile computing device, a smartphone, a tablet computer, a pager, a laptop, a local router, a data recorder, a network hub, a server, a secondary mobile computing device, a repeater, a combination thereof, or the like.

In aspects, a system in accordance with the present disclosure may include a plurality of substantially similar modules (e.g., generally interchangeable modules, but with unique identifiers), for coupling with a plurality of patches, each patch optionally different from the other patches in the system (e.g., potentially including alternative sensors, sensor types, sensor configurations, electrodes, electrode configurations, etc.). Each patch may include an interconnect suitable for attachment to an associated module. Upon attachment of a module to a corresponding patch, the module may validate the type and operation of the patch to which it has been mated. In aspects, the module may then initiate monitoring operations on the subject via the attached patch, communicate with one or more other patches on the subject, a hub, etc. The data collection from each module may be coordinated through one or more modules and/or with a host device in accordance with the present disclosure. The modules may report a timestamp along with the data in order to synchronize data collection across multiple patch-module pairs on the subject, between subjects, etc. Thus, if a module is to be replaced, a hot swappable replacement (e.g., replacement during a monitoring procedure) can be carried out easily by the subject, a caregiver, practitioner, etc. during the monitoring process. Such a configuration may be advantageous for performing redundant, continuous monitoring of a subject, and/or to obtain spatially relevant information from a plurality of locations on the subject during use.

In aspects, the modules and/or patches may include corresponding interconnects for coupling with each other during use. The interconnects may include one or more connectors, configured such that the modules and patches may only couple in a single unique orientation with respect to each other. In aspects, the modules may be color coded by function. A temporary stiffening element attached to a patch may include instructions, corresponding color coding, etc. so as to assist a user or subject with simplifying the process of monitoring.

In addition to physiologic monitoring, one or more patches and/or modules may be used to provide a stimulus to the subject, as will be described in further detail below.

According to aspects there is provided use of a modular physiologic monitoring system in accordance with the present disclosure to monitor a subject, to monitor an electrocardiogram (EKG) of a subject, to perform one or more tasks in accordance with the present disclosure, etc.

According to aspects there is provided an interface (e.g., a patch in accordance with the present disclosure) for monitoring a physiologic, physical, and/or electrophysiological signal from a subject. The interface or patch may include a substrate, an adhesive coupled to the substrate formulated for attachment to the skin of a subject, and one or more sensors and/or electrodes each in accordance with the present disclosure coupled to the substrate, arranged, configured, and dimensioned to interface with the subject. The substrate may be formed from an elastic or polymeric material, such that the patch is configured to maintain operation when stretched to more than 25%, more than 50%, or more than 80%.

According to aspects there is provided an isolating patch for providing a barrier between a handheld monitoring device with a plurality of contact pads and a subject, including a flexible substrate with two surfaces, a patient facing surface and an opposing surface, and an electrically and/or ionically conducting adhesive coupled to at least a portion of the patient facing surface configured so as to electrically and mechanically couple with the subject when placed thereupon, wherein the conducting adhesive is exposed within one or more regions of the opposing surface of the substrate, the regions patterned so as to substantially match the dimensions and layout of the contact pads. In aspects, the conducting adhesive may include an anisotropically conducting adhesive, with the direction of conduction oriented substantially normal to the surfaces of the substrate.

In aspects, the adhesive may be patterned onto the substrate so as to form one or more exposed regions of the substrate, one or more of the sensors and/or electrodes arranged within the exposed regions. One or more of the electrodes may include an inherently or ionically conducting gel adhesive.

In aspects, one or more of the electrodes may include an electrode feature arranged so as to improve the electrical connection between the electrode and the skin upon placement on a subject. In aspects, the improved electrical connection may be achieved after pressure is applied to the electrode (e.g., after the patch is secured to the subject and then a pressure is applied to the electrode). The electrode feature may include one or more microfibers, barbs, microneedles, or spikes to penetrate into a stratum corneum of the skin. The electrode feature may be configured to penetrate less than 2 mm into the skin, less than 1 mm, less than 0.5 mm, less than 0.2 mm, or the like during engagement therewith. In aspects, a gel adhesive in accordance with the present disclosure located adjacent to the electrode features (e.g., between the features and the skin) may be configured to maintain the improved electrical connection to the skin for more than 1 hr, more than 1 day, or more than 3 days after the electrode contacts the skin or pressure is applied to the electrode.

In aspects, a patch interface in accordance with the present disclosure may include one or more stretchable electrically conducting traces attached to the substrate, arranged so as to couple one or more of the sensors and/or electrodes with one or more of the interconnects.

In aspects, the interconnect may include a plurality of connectors, the connectors physically connected to each other through the substrate. The patch may include an isolating region arranged so as to isolate one or more of the connectors from the skin while the patch is engaged therewith According to aspects there is provided a device (e.g., a module in accordance with the present disclosure) for monitoring a physiologic, physical, and/or electrophysiological signal from a subject. The module may include a housing, a printed circuit board (PCB) including one or more microcircuits, and an interconnect configured for placement of the device onto a subject interface (e.g., a patch in accordance with the present disclosure). The PCB may constitute at least a portion of the housing in some embodiments. The module may include a three-dimensional antenna coupled to the microcircuits (e.g., coupled with a transceiver, transmitter, radio, etc. included within the microcircuits). In aspects, the antenna may be printed onto or embedded into the housing. In aspects, the antenna may be printed on an interior wall of or embedded into the housing, the circuit board providing a ground plane for the antenna. In aspects, the housing may be shaped like a dome and the antenna may be patterned into a spiraling helix centered within the dome.

In aspects, a module in accordance with the present disclosure may include a sensor coupled with one or more of the microcircuits, the sensor configured to interface with one of the subject upon attachment of the module to the patch interface. The module may include a sensor and/or microelectronics configured to interface with a sensor included on a corresponding patch interface. In aspects, one or more of the sensors may include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, a combination thereof, or the like.

In aspects, the module may be hermetically sealed. The module and/or patch interface may include a gasket coupled to the circuit board or the substrate, the gasket formed so as to isolate the region formed by the module interconnect and the patch from a surrounding environment, when the module is coupled with the patch.

In aspects, the module interconnect may include an electrically conducting magnetic element, and the patch interface may include one or more ferromagnetic regions coupled to the substrate, the magnetic elements arranged so as to physically and/or electrically couple the module to the patch interface when the magnetic elements are aligned with the ferromagnetic regions. In aspects, the ferromagnetic regions may be formed from stretchable pseudo elastic material and/or may be printed onto the substrate. In aspects, the module and/or the patch interface may include one or more fiducial markings to visually assist with the alignment of the module to the patch during coupling thereof.

According to aspects there is provided a kit for monitoring a physiologic, physical, and/or electrophysiological signal from a subject, including one or more patches in accordance with the present disclosure, one or more modules in accordance with the present disclosure, a recharging bay in accordance with the present disclosure, and one or more accessories in accordance with the present disclosure. One or more of the accessories may include an adhesive removing agent configured to facilitate substantially pain free removal of one or more of the patches from a subject.

According to aspects there is provided a service system for managing the collection of physiologic data from a customer, including a customer data management service, configured to generate and/or store the customer profile referencing customer preferences, data sets, and/or monitoring sessions, an automated product delivery service configured to provide the customer with one or more monitoring products or supplies in accordance with the present disclosure, and a datacenter configured to store, analyze, and/or manage the data obtained from the customer during one or more monitoring sessions.

In aspects, the service system may include a report generating service configured to generate one or more monitoring reports based upon the data obtained during one or more monitoring sessions, a report generating service coupled to the datacenter configured to generate one or more monitoring reports based upon the data obtained during one or more monitoring sessions, and/or a recurrent billing system configured to bill the customer based upon the number or patches consumed, the data stored, and/or the reports generated throughout the course of one or more monitoring sessions.

According to aspects there is provided a method for monitoring one or more physiologic and/or electrophysiological signals from a subject, including attaching one or more soft breathable and hypoallergenic devices to one or more sites on the subject, obtaining one or more local physiologic and/or electrophysiological signals from each of the devices, and analyzing the signals obtained from each of the devices to generate a metric, diagnostic, report, and/or additional signals therefrom.

In aspects, the method may include hot swapping one or more of the devices without interrupting the step of obtaining, and/or calibrating one or more of the devices while on the subject. In aspects, the step of calibrating may be performed with an additional medical device (e.g., a blood pressure cuff, a thermometer, a pulse oximeter, a cardiopulmonary assessment system, a clinical grade EKG diagnostic system, etc.).

In aspects, the method may include determining the position and/or orientation of one or more of the devices on the subject, and/or determining the position and/or orientation from a photograph, a video, or a surveillance video.

In aspects, one or more steps of a method in accordance with the present disclosure may be performed at least in part by a device, patch interface, module, and/or system each in accordance with the present disclosure.

According to aspects there is provided a system for measuring blood pressure of a subject in an ambulatory setting including an EKG device in accordance with the present disclosure (e.g., a patch/module pair in accordance with the present disclosure configured to measure local electrophysiological signals in adjacent tissues), configured for placement onto a torso of the subject, the EKG device configured to measure an electrocardiographic signal from the torso of the subject so as to produce an EKG signal, one or more pulse devices (e.g., patch/module pairs in accordance with the present disclosure configured to measure local blood flow in adjacent tissues) each in accordance with the present disclosure, configured for placement onto one or more sites on one or more extremities of the subject, each of the pulse devices configured to measure a local pulse at the placement site so as to produce one or more pulse signals; and a processor included in or coupled to one or more of the EKG device and the pulse devices, the processor configured to receive the EKG signal, the pulse signals, and/or signals generated therefrom, the processor including an algorithm, the algorithm configured to analyze one or more temporal metrics from the signals in combination with one or more calibration parameters, to determine the blood pressure of the subject.

In aspects, the system for monitoring blood pressure of a subject may include a blood pressure cuff configured to produce a calibration signal, the processor configured to generate one or more of the calibration parameters, from the calibration signal in combination with the EKG signal, and pulse signals.

In aspects, one or more of the devices may include an orientation sensor, the orientation sensor configured to obtain an orientation signal, the processor configured to receive the orientation signal or a signal generated therefrom, and to incorporate the orientation signal into the analysis. Some non-limiting examples of orientation sensors include one or more of an altimeter, a barometer, a tilt sensor, a gyroscope, combinations thereof, or the like.

A system for measuring the effect of an impact on physiologic state of a subject including an electroencephalogram (EEG) device (e.g., a patch/module pair in accordance with the present disclosure configured to measure local electrophysiological signals associated with brain activity in adjacent tissues) in accordance with the present disclosure, configured for placement behind an ear, on the forehead, near a temple, onto the neck of the subject, or the like, the EEG device configured to measure an electroencephalographic signal from the head of the subject so as to produce an EEG signal, and configured to measure one or more kinetic and/or kinematic signals from the head of the subject so as to produce an impact signal, and a processor included in or coupled to the EEG device, the processor configured to receive the EEG signal, the impact signals, and/or signals generated therefrom, the processor including an algorithm, the algorithm configured to analyze the impact signals to determine if the subject has suffered an impact, to separate the signals into pre impact and post impact portions and to compare the pre and post impact portions of the EEG signal, to determine the effect of the impact on the subject.

In aspects, the EEG device may include additional sensors such as a temperature sensor configured to generate a temperature signal from the subject or a signal generated therefrom, the processor configured to receive the temperature signal and to assess a thermal state of the subject therefrom. In aspects, the EEG device may include a hydration sensor configured to generate a fluid level signal from the subject, the processor configured to receive the fluid level signal or a signal generated therefrom, and to assess the hydration state of the subject therefrom.

In aspects, the EEG device and/or the processor may include or be coupled to a memory element, the memory element including sufficiently large space to store the signals for a period of 3 minutes, 10 minutes, 30 minutes, or 1 hour.

In aspects, the system for measuring the effect of an impact on physiologic state of a subject may include an EKG device (e.g., a patch/module pair in accordance with the present disclosure configured to measure local electrophysiological signals in adjacent tissues) in accordance with the present disclosure, the EKG device configured for placement onto the torso or neck of the subject, the EKG device configured to measure an electrophysiological signal pertaining to cardiac function of the subject so as to produce an EKG signal, the processor configured to receive the EKG signal or a signal generated therefrom, the algorithm configured so as to incorporate the EKG signal into the assessment. In aspects, the processor may be configured to extract a heart rate variability (HRV) signal from the EKG signal, a pre impact and post impact portion of the HRV signal compared to determine at least a portion of the effect of the impact.

According to aspects there is provided a system for assessing a sleep state of a subject including an electromyography (EMG)/electrooculography (EOG) device (e.g., a patch/module pair in accordance with the present disclosure configured to measure local electromyographic and/or electrooculographic signals from adjacent tissues), in accordance with the present disclosure, configured for placement behind an ear, on a forehead, substantially around an eye, near a temple, or onto a neck of the subject, the EMG/EOG device configured to measure one or more electromyographic and/or electrooculographic signals from the head or neck of the subject so as to produce an EMG/EOG signal, and a processor included in or coupled to the EMG/EOG device, the processor configured to receive the EMG/EOG signal, and/or signals generated therefrom, the processor including an algorithm, the algorithm configured to analyze EMG/EOG signal, to determine the sleep state of the subject.

In aspects, the EMG/EOG device may include a microphone, the microphone configured to obtain an acoustic signal from the subject, the processor configured to receive the acoustic signal or a signal generated therefrom, the algorithm configured so as to incorporate the acoustic signal into the assessment.

In aspects, the system may include a sensor for evaluating oxygen saturation (SpO2) at one or more sites on the subject to obtain an oxygen saturation signal from the subject, the processor configured to receive the oxygen saturation signal or a signal generated therefrom, the algorithm configured so as to incorporate the oxygen saturation signal into the assessment.

In aspects, the processor may include a signal analysis function, the signal analysis function configured to analyze the EMG/EOG signals, the acoustic signal, and/or the oxygen saturation signal to determine the sleep state of the subject, identify snoring, identify a sleep apnea event, identify a bruxism event, identify a rapid eye movement (REM) sleep state, identify a sleep walking state, a sleep talking state, a nightmare, or identify a waking event. In aspects, the system may include a feedback mechanism, configured to interact with the subject, a user, a doctor, a nurse, a partner, a combination thereof, or the like. The processor may be configured to provide a feedback signal to the feedback mechanism based upon the analysis of the sleep state of the subject. The feedback mechanism may include a transducer, a loudspeaker, tactile actuator, a visual feedback means, a light source, a buzzer, a combination thereof, or the like to interact with the subject, the user, the doctor, the nurse, the partner, or the like.

A modular physiologic monitoring system, in some embodiments, includes one or more sensing devices, which may be placed or attached to one or more sites on the subject. Alternatively or additionally, one or more sensing devices may be placed "off" the subject, such as one or more sensors (e.g., cameras, acoustic sensors, etc.) that are not physically attached to the subject. The sensing devices are utilized to establish whether or not an event is occurring and to determine one or more characteristics of the event by monitoring and measuring physiologic parameters of the subject. The determination of whether an event has occurred or is occurring may be made by a device that is at least partially external and physically distinct from the one or more sensing devices, such as a host device in wired or wireless communication with the sensing devices as described below with respect to FIG. 1. The modular physiologic monitoring system includes one or more stimulating devices, which again may be any combination of devices that are attached to the subject or placed "off" the subject, to apply a stimulus to the subject in response to a detected event. Various types of stimulus may be applied, including but not limited to stimulating via thermal input, vibration input, mechanical input, a compression or the like with an electrical input, etc.

The sensing devices of a modular physiologic monitoring system, such as patch-module pairs described below with respect to FIG. 1, may be used to monitor one or more physiologic functions or parameters of a subject, as will be described in further detail below. The sensing devices of the modular physiologic monitoring system, or a host device configured to receive data or measurements from the sensing devices, may be utilized to monitor for one or more events (e.g., through analysis of signals measured by the sensing devices, from metrics derived from the signals, etc.). The stimulating devices of the modular physiologic monitoring system may be configured to deliver one or more stimuli (e.g., electrical, vibrational, acoustic, visual, etc.) to the subject. The stimulating devices may receive a signal from one or more of the sensing devices or a host device, and provide the stimulation in response to the received signal.

FIG. 1 shows aspects of a modular physiologic monitoring system in accordance with the present disclosure. In FIG. 1, a subject 1 is shown with a number of patches and/or patch-module pairs each in accordance with the present disclosure attached thereto at sites described below, a host device 145 in accordance with the present disclosure, a feedback/user device 147 in accordance with the present disclosure displaying some data 148 based upon signals obtained from the subject 1, and one or more feedback devices 135, 140, in accordance with the present disclosure configured to convey to the subject 1 one or more aspects of the signals or information gleaned therefrom. In some embodiments, the feedback devices 135, 140 may also or alternatively function as stimulating devices. The host device 145, the user device 147, the patches and/or patch-module pairs, and/or the feedback devices 135, 140 may be configured for wireless communication 146, 149 during a monitoring session.

In aspects, a patch-module pair may be adapted for placement almost anywhere on the body of a subject 1. As shown in FIG. 1, some sites may include attachment to the cranium or forehead 131, the temple, the ear or behind the ear 50, the neck, the front, side, or back of the neck 137, a shoulder 105, a chest region with minimal muscle mass 100, integrated into a piece of ornamental jewelry 55 (may be a host, a hub, a feedback device, etc.), arrangement on the torso 110a-c, arrangement on the abdomen 80 for monitoring movement or breathing, below the rib cage 90 for monitoring respiration (generally on the right side of the body to substantially reduce EKG influences on the measurements), on a muscle such as a bicep 85, on a wrist 135 or in combination with a wearable computing device 60 on the wrist (e.g., a smart watch, a fitness band, etc.), on a buttocks 25, on a thigh 75, on a calf muscle 70, on a knee 35 particularly for proprioception based studies and impact studies, on a shin 30 primarily for impact studies, on an ankle 65, over an Achilles tendon 20, on the front or top of the foot 15, on a heel 5, or around the bottom of a foot or toes 10. Other sites for placement of such devices are envisioned. Selection of the monitoring and/or stimulating sites is generally determined based upon the intended application of the patch-module pairs described herein.

Additional placement sites on the abdomen, perineal region 142a-c, genitals, urogenital triangle, anal triangle, sacral region, inner thigh 143, or the like may be advantageous in the assessment of autonomic neural function of a subject. Such placements regions may be advantageous for assessment of parasympathetic nervous system (PNS) activity, somatosensory function, assessment of sympathetic nervous system (SNS) functionality, etc.

Placement sites on the wrist 144*a*, hand 144*b* or the like may advantageous for interacting with a subject, such as via performing a stress test, performing a thermal stress test, performing a tactile stress test, monitoring outflow, afferent traffic, efferent traffic, etc.

Placement sites on the nipples, areola, lips, labia, clitoris, penis, the anal sphincter, levator ani muscle, over the ischiocavernous muscle, deep transverse perineal muscle, *labium minus, labium majus*, one or more nerves near the surface thereof, posterior scrotal nerves, perineal membrane, perineal nerves, superficial transverse perineal nerves, dorsal nerves, inferior rectal nerves, etc. may be advantageous for assessment of autonomic neural ablation procedures, autonomic neural modulation procedures, assessment of the PNS of a subject, assessment of sexual dysfunction of a subject, etc.

Placement sites on the face 141, over ocular muscles, near the eye, over a facial muscle (e.g., a nasalis, temporalis, zygonaticus minor/major, orbicularis oculi, occipitofrontalis), near a nasal canal, over a facial bone (e.g., frontal process, zygomatic bone/surface, zygomaticofacial foreman, malar bone, nasal bone, frontal bone, maxilla, temporal bone, occipital bone, etc.), may be advantageous to assess ocular function, salivary function, sinus function, interaction with the lips, interaction with one or more nerves of the PNS (e.g., interacting with the vagus nerve within, on, and/or near the ear of the subject), etc.

In aspects, a system in accordance with the present disclosure may be configured to monitor one or more physiologic parameters of the subject 1 before, during, and/or after one or more of, a stress test, consumption of a medication, exercise, a rehabilitation session, a massage, driving, a movie, an amusement park ride, sleep, intercourse, a surgical, interventional, or non-invasive procedure, a neural remodeling procedure, a denervation procedure, a sympathectomy, a neural ablation, a peripheral nerve ablation, a radio-surgical procedure, an interventional procedure, a cardiac repair, administration of an analgesic, a combination thereof, or the like. In aspects, a system in accordance with the present disclosure may be configured to monitor one or more aspects of an autonomic neural response to a procedure, confirm completion of the procedure, select candidates for a procedure, follow up on a subject after having received a procedure, assess the durability of a procedure, or the like (e.g., such as wherein the procedure is a renal denervation procedure, a carotid body denervation procedure, a hepatic artery denervation procedure, a LUTs treatment, a bladder denervation procedure, a urethral treatment, a prostate ablation, a prostate nerve denervation procedure, a cancer treatment, a pain block, a neural block, a bronchial denervation procedure, a carotid sinus neuromodulation procedure, implantation of a neuromodulation device, tuning of a neuromodulation device, etc.).

Additional details regarding modular physiologic monitoring systems, kits and methods are further described in PCT application serial no. PCT/US2014/041339, published as WO 2014/197822 and titled "Modular Physiologic Monitoring Systems, Kits, and Methods," PCT application serial no. PCT/US2015/043123, published as WO 2016/019250 and titled "Modular Physiologic Monitoring Systems, Kits, and Methods," and PCT application serial no. PCT/US2017/030186, published as WO 2017/190049 and titled "Monitoring and Management of Physiologic Parameters of a Subject," the disclosures of which are incorporated by reference herein in their entirety.

In some embodiments, modular physiologic monitoring systems may include sensing and stimulating devices that are physically distinct, such as sensing and stimulating devices that are physically attached to a subject at varying locations. For example, the sensing and stimulating devices may include different ones of the patch-module pairs described above with respect to FIG. 1. In other embodiments, one or more devices may provide both monitoring and stimulating functionality. For example, one or more of the patch-module pairs described above with respect to FIG. 1 may be configured to function as both a sensing device and a stimulating device. It is to be appreciated, however, that embodiments are not limited solely for use with the patch-module pairs of FIG. 1 as sensing and stimulating devices. Various other types of sensing and stimulating devices may be utilized, including but not limited to sensors that are "off-body" with respect to subject 1.

The sensing and/or stimulating devices of a modular physiologic monitoring system may be configured for radio frequency (RF) or other wireless and/or wired connection with one another and/or a host device. Such RF or other connection may be used to transmit or receive feedback parameters or other signaling between the sensing and stimulating devices. The feedback, for example, may be provided based on measurements of physiologic parameters that are obtained using the sensing devices to determine when events related to cardiac output are occurring. Various thresholds for stimulation that are applied by the stimulating devices may, in some embodiments, be determined based on such feedback. Thresholds may relate to the amplitude or frequency of electric or other stimulation. Thresholds may also be related to whether to initiate stimulation by the stimulating devices based on the feedback.

During and/or after stimulus is applied with the stimulating devices, the sensing devices may monitor the physiologic response of the subject. If stimulation is successful in achieving a desired response, the stimulation may be discontinued. Otherwise, the type, timing, etc. of stimulation may be adjusted.

In some embodiments, a user of the modular physiologic monitoring system may set preferences for the stimulus type, level, and/or otherwise personalize the sensation during a setup period or at any point during use of the modular physiologic monitoring system. The user of the modular physiologic monitoring system may be the subject being monitored and stimulated by the sensing devices and stimulating devices, or a doctor, nurse, physical therapist, medical assistant, caregiver, etc. of the subject being monitored and stimulated. The user may also have the option to disconnect or shut down the modular physiologic monitoring system at any time, such as via operation of a switch, pressure sensation, voice operated instruction, etc.

Stimulus or feedback which may be provided via one or more stimulating devices in a modular physiologic monitoring system may be in various forms, including physical stimulus (e.g., electrical, thermal, vibrational, pressure, stroking, a combination thereof, or the like), optical stimulus, acoustic stimulus, etc.

Physical stimulus may be provided in the form of negative feedback, such as in a brief electric shock or impulse as described above. Data or knowledge from waveforms applied in conducted electrical weapons (CEWs), such as in electroshock devices, may be utilized to avoid painful stimulus. Physical stimulus may also be provided in the form of positive feedback, such as in evoking pleasurable sensations by combining non-painful electrical stimulus with pleasant sounds, music, lighting, smells, etc. Physical stimulus is not limited solely to electrical shock or impulses. In other embodiments, physical stimulus may be provided by adjusting temperature or other stimuli, such as in providing a burst of cool or warm air, a burst of mist, vibration, tension, stretch, pressure, etc.

Feedback provided via physical stimulus as well as other stimulus described herein may be synchronized with, initiated by or otherwise coordinated or controlled in conjunction with one or more monitoring devices (e.g., a host device, one or more sensing devices, etc.). The monitoring devices may be connected to the stimulating devices physically (e.g., via one or more wires or other connectors), wirelessly (e.g., via radio or other wireless communication), etc. Physical stimulus may be applied to various regions of a subject, including but not limited to the wrist, soles of the feet, palms of the hands, nipples, forehead, ear, mastoid region, the skin of the subject, etc.

Optical stimulus may be provided via one or more stimulating devices. The optical stimulus may be positive or negative (e.g., by providing pleasant or unpleasant lighting or other visuals). Acoustic stimulus similarly may be provided via one or more stimulating devices, as positive or negative feedback (e.g., by providing pleasant or unpleasant sounds). Acoustic stimulus may take the form of spoken words, music, etc. Acoustic stimulus, in some embodiments may be provided via smart speakers or other electronic devices such as Amazon Echo®, Google Home®, Apple Home Pod®, etc. The stimulus itself may be provided so as to elicit a particular psychophysical or psychoacoustic effect in the subject, such as directing the subject to stop an action, to restart an action (such as breathing), to adjust an action (such as a timing between a step and a respiratory action, between a muscle contraction and a leg position, etc.).

As described above, the modular physiologic monitoring system may operate in a therapeutic mode, in that stimulation is provided when one or more cardiac parameters of a subject indicate some event (e.g., actual, imminent or predicted failure or worsening). The modular physiologic monitoring system, however, may also operate as or provide a type of cardiac "pacemaker" in other embodiments. In such embodiments, the modular physiologic monitoring system has the potential to reduce the frequency of cardiac events, or to possibly avoid certain cardiac events altogether. A modular physiologic monitoring system may provide functionality for timing and synchronizing periodic compression and relaxation of microvascular blood vessel networks with cardiac output. Such techniques may be utilized to respond to a type of failure event as indicated above. Alternatively or additionally, such techniques may be provided substantially continuously, so as to improve overall cardiac performance (e.g., blood flow) with the same or less cardiac work.

In some embodiments, a modular physiologic monitoring system may be configured to provide multi-modal stimuli to a subject. Multi-modal approaches use one or more forms of stimulation (e.g., thermal and electrical, mechanical and electrical, etc.) in order to mimic another stimulus to trick local nerves into responding in the same manner to the mimicked stimulus. In addition, in some embodiments multi-modal stimulus or input may be used to enhance a particular stimulus. For example, adding a mimicked electrical stimulus may enhance the effect of a thermal stimulus.

Modular physiologic monitoring systems may use pulses across space and time (e.g., frequency, pulse trains, relative amplitudes, etc.) to mimic vibration, comfort or discomfort, mild or greater pain, wet sensation, heat/cold, training neuroplasticity, taste (e.g., using a stimulating device placed in the mouth or on the tongue of a subject to mimic sour, sweet, salt, bitter or umami flavor), tension or stretching, sound or acoustics, sharp or dull pressure, light polarization (e.g., linear versus polar, the "Haidinger Brush"), light color or brightness, etc.

Stimulus amplification may also be provided by one or more modular physiologic monitoring systems using multi-modal input. Stimulus amplification represents a hybrid approach, wherein a first type of stimulus may be applied and a second, different type of stimulus provided to enhance the effect of the first type of stimulus. As an example, a first stimulus may be provided via a heating element, where the heating element is augmented by nearby electrodes or other stimulating devices that amplify and augment the heating stimulus using electrical mimicry in a pacing pattern. Electrical stimulus may also be used as a supplement or to mimic various other types of stimulus, including but not limited to vibration, heat, cold, etc. Different, possibly unique, stimulation patterns may be applied to the subject, with the central nervous system and peripheral nervous system interpreting such different or unique stimulation patterns as different stimulus modalities.

Another example of stimulus augmentation is sensing a "real" stimulus, measuring the stimulus, and constructing a proportional response by mimicry such as using electric pulsation. The real stimulus, such as sensing heat or cold from a Peltier device, may be measured by electrical-thermal conversion. This real stimulus may then be amplified using virtual mimicry, which may provide energy savings and the possibility of modifying virtual stimulus to modify the perception of the real stimulus.

In some embodiments, the stimulating devices in a modular physiologic monitoring system include an electrode array that attaches (e.g., via an adhesive or which is otherwise held in place) to a preferred body part. One or more of the stimulating devices may include a multiplicity of both sensing and stimulation electrodes, including different types of sensing and/or stimulation electrodes. The sensing electrodes on the stimulation devices, in some embodiments, may be distinct from the sensing devices in the modular physiologic monitoring system in that the sensing devices in the modular physiologic monitoring system may be used to measure physiologic parameters of the subject while the sensing electrodes on the stimulation devices in the modular physiologic monitoring system may be utilized to monitor the application of a stimulus to the subject.

A test stimulus may be initiated in a pattern in the electrode array, starting from application via one or a few of the stimulation electrodes and increasing in number over time to cover an entire or larger portion of the electrode array. The test stimulus may be used to determine the subject's response to the applied stimulation. Sensing electrodes on the stimulation devices may be used to monitor the application of the stimulus. The electrode array may also be used to record a desired output (e.g., physiologic parameters related to cardiac output). As such, one or more of the electrodes in the array may be configured so as to measure the local evoked response associated with the stimulus itself. Such an approach may be advantageous to confirm capture of the target nerves during use. By monitoring the neural response to the stimulus, the stimulus parameters including amplitude, duration, pulse number, etc. may be adjusted while ensuring that the target nerves are enlisted by the stimulus in use.

The test stimulus may migrate or be applied in a pattern to different electrodes at different locations in the electrode array. The response to the stimulus may be recorded or otherwise measured, using the sensing devices in the modular physiologic monitoring system and/or one or more of the sensing electrodes of the stimulating devices in the modular physiologic monitoring system. The response to the test stimulus may be recorded or analyzed to determine an optimal sensing or application site for the stimulus to achieve a desired effect or response in the subject. Thus, the test stimulus may be utilized to find an optimal sensing (e.g., dermatome driver) location. This allows for powerful localization for optimal pacing or other application of stimulus, which may be individualized for different subjects.

A stimulating device applied to the subject via an adhesive (e.g., an adhesively applied stimulating device), may be in the form of a disposable or reusable unit, such as a patch and or patch-module or patch/hub pair as described above with respect to FIG. 1. An adhesively applied stimulating device, in some embodiments, includes a disposable interface configured so as to be thin, stretchable, able to conform to the skin of the subject, and sufficiently soft for comfortable wear. The disposable interface may be built from very thin, stretchable and/or breathable materials, such that the subject generally does not feel the device on his or her body.

The adhesively applied stimulating device also includes a means for interfacing with the subject through an adhesive interface and/or a window in the adhesive interface. Such means may include a plurality of electrodes that are coupled with a reusable component of the adhesively applied stimulating device and that are coupled to the body of the subject through the adhesive interface. The means may also or alternatively include: a vibrating actuator to provide vibration normal to and/or transverse to the surface of the skin on which the adhesively applied stimulating device is attached to the subject; a thermal device such as a Peltier device, a heating element, a cooling element, an RF heating circuit, an ultrasound source, etc.; a means for stroking the skin such as a shape memory actuator, an electroactive polymer actuator, etc.; a means for applying pressure to the skin such as a pneumatic actuator, a hydraulic actuator, etc.

Actuation means of the adhesively applied stimulating device may be applied over a small region of the applied area of the subject, such that the adhesive interface provides the biasing force necessary to counter the actuation of the actuation means against the skin of the subject.

Adhesively applied stimulating devices may be provided as two components—a disposable body interface and a reusable component. The disposable body interface may be applied so as to conform to the desired anatomy of the subject, and wrap around the body such that the reusable component may interface with the disposable component in a region that is open and free from a natural interface between the subject and another surface.

An adhesively applied stimulating device may also be a single component, rather than a two component or other multi-component arrangement. Such a device implemented as a single component may include an adhesive interface to the subject including two or more electrodes that are applied to the subject. Adhesively applied stimulating devices embodied as a single component provide potential advantages such as easier application to the body of the subject, but may come at a disadvantage with regards to one or more of breathability, conformity, access to challenging interfaces, etc. relative to two component or multi-component arrangements.

A non-contacting stimulating device may be, for example an audio and/or visual system, a heating or cooling system, etc. Smart speakers and smart televisions or other displays are examples of audio and/or visual non-contacting stimulation devices. A smart speaker, for example, may be used to provide audible stimulus to the subject in the form of an alert, a suggestion, a command, music, other sounds, etc. Other examples of non-contacting stimulating devices include means for controlling temperature such as fans, air conditioners, heaters, etc.

One or more stimulating devices may also be incorporated in other systems, such as stimulating devices integrated into a bed, chair, operating table, exercise equipment, etc. that a subject interfaces with. A bed, for example, may include one or more pneumatic actuators, vibration actuators, shakers, or the like to provide a stimulus to the subject in response to a command, feedback signal or control signal generated based on measurement of one or more physiologic parameters of the subject utilizing one or more sensing devices.

Although the disclosure has discussed devices attached to the body for monitoring aspects of the subject's disorder and/or physiologic information, as well as providing a stimulus, therapeutic stimulus, etc. alternative devices may be considered. Non-contacting devices may be used to obtain movement information, audible information, skin blood flow changes (e.g., such as by monitoring subtle skin tone changes which correlate with heart rate), respiration (e.g., audible sounds and movement related to respiration), and the like. Such non-contacting devices may be used in place of or to supplement an on-body system for the monitoring of certain conditions, for applying stimulus, etc. Information captured by non-contacting devices may, on its own or in combination with information gathered from sensing devices on the body, be used to direct the application of stimulus to the subject, via one or more stimulating devices on the body and/or via one or more non-contacting stimulating devices.

In some embodiments, aspects of monitoring the subject utilizing sensing devices in the modular physiologic monitoring system may utilize sensing devices that are affixed to or embodied within one or more contact surfaces, such as surfaces on a piece of furniture on which a subject is positioned (e.g., the surface of a bed, a recliner, a car seat, etc.). The surface may be equipped with one or more sensors to monitor the movement, respiration, HR, etc. of the subject. To achieve reliable recordings, it is advantageous to have such surfaces be well positioned against the subject. It is also advantageous to build such surfaces to take into account comfort level of the subject to keep the subject from feeling the sensing surfaces and to maintain use of the sensing surface over time.

Stimulating devices, as discussed above, may take the form of audio, visual or audiovisual systems or devices in the sleep space of the subject. Examples of such stimulating devices include smart speakers. Such stimulating devices provide a means for instruction a subject to alter the sleep state thereof. The input or stimulus may take the form of a message, suggestion, command, audible alert, musical input, change in musical input, a visual alert, one or more lights, a combination of light and sound, etc. Examples of such non-contacting stimulating devices include systems such as Amazon Echo®, Google Home®, Apple Home Pod®, and the like.

Figure 2A:
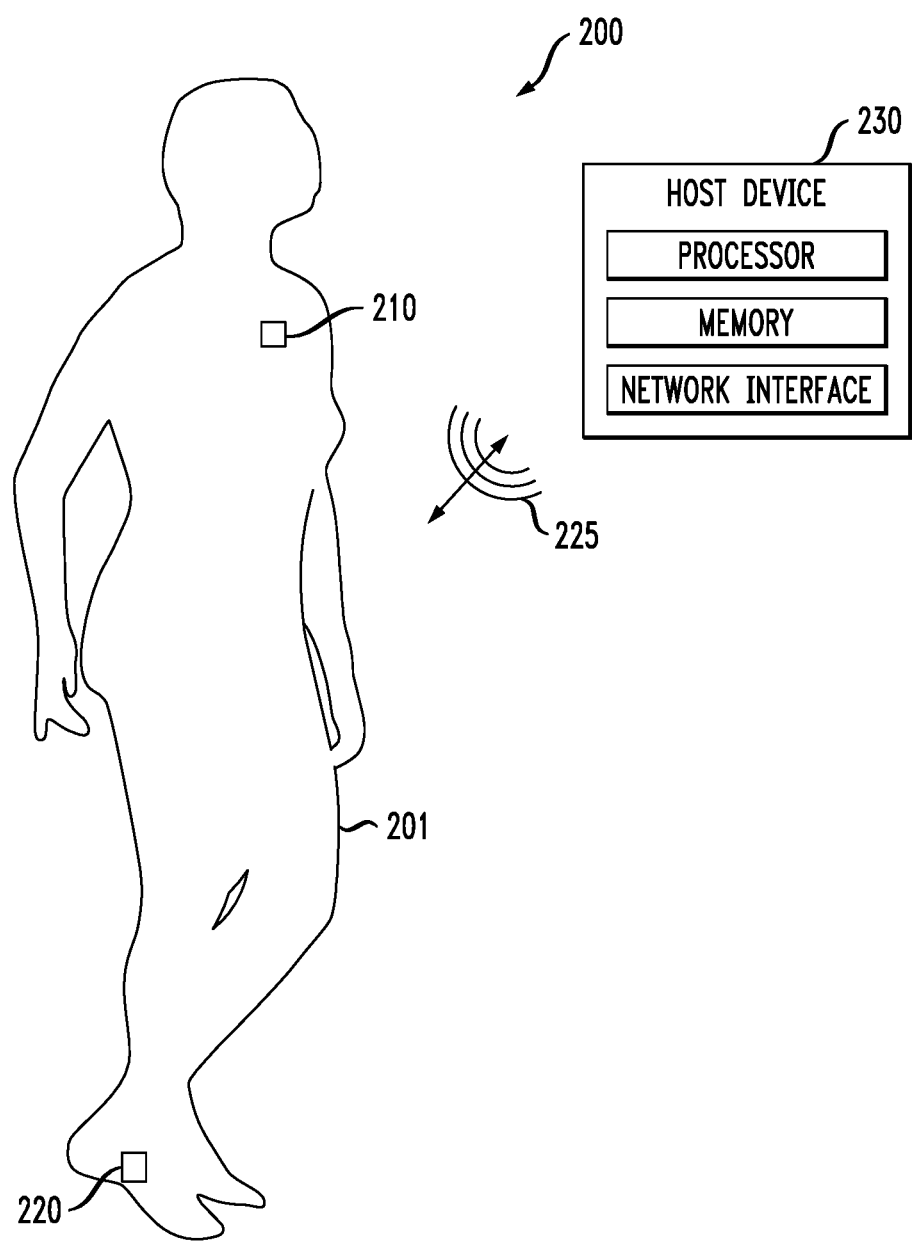
FIGS. 2A-2C illustrate a modular physiologic monitoring system, according to an embodiment of the invention.
Figure 2B:
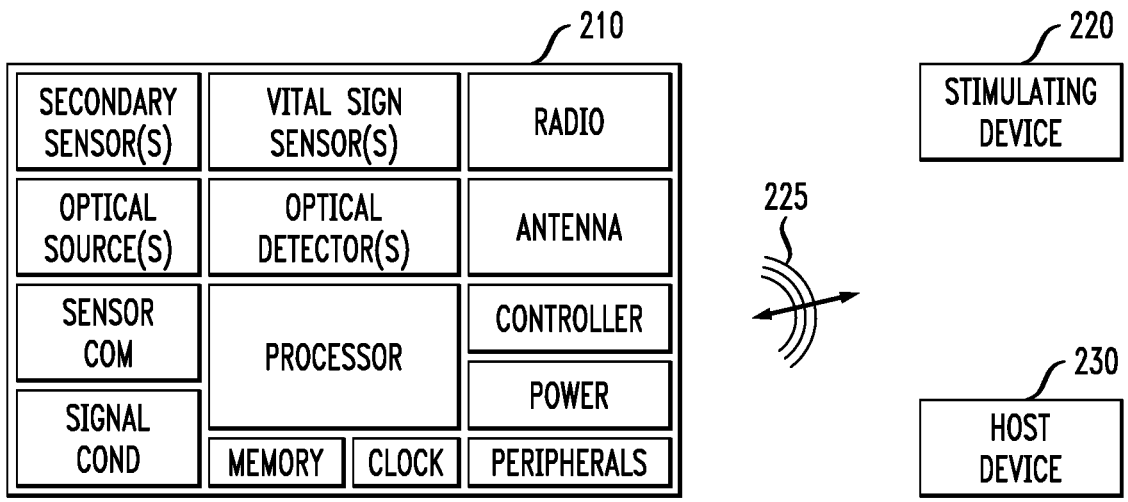
Figure 2C:
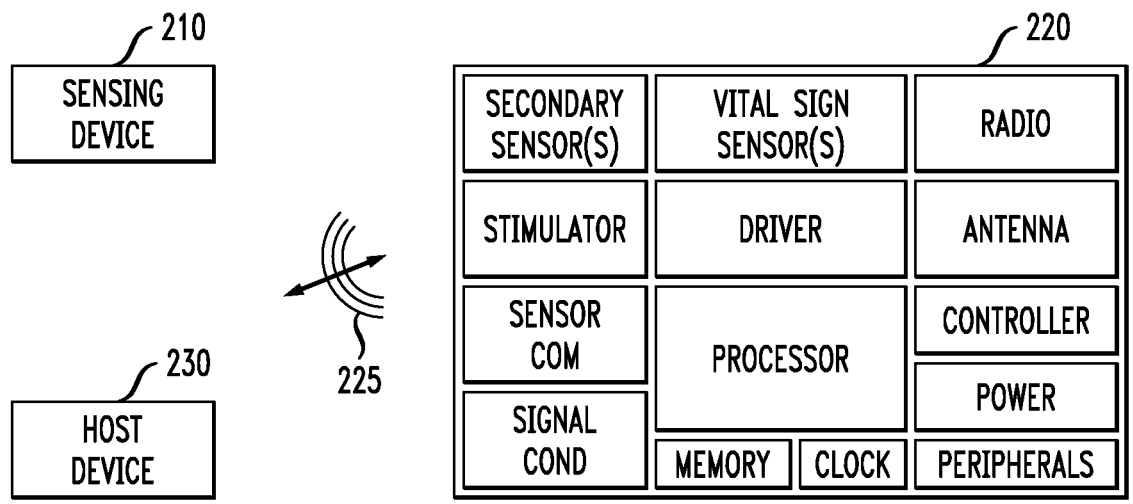

FIGS. 2A-2C show a modular physiologic monitoring system 200. The modular physiologic monitoring system 200 includes a sensing device 210 and a stimulating device 220 attached to a subject 201 that are in wireless communication 225 with a host device 230. The host device 230 includes a processor, a memory and a network interface.

The processor may comprise a microprocessor, a microcontroller, an application-specific integrated circuit (ASIC), a field-programmable gate array (FPGA) or other type of processing circuitry, as well as portions or combinations of such circuitry elements.

The memory may comprise random access memory (RAM), read-only memory (ROM) or other types of memory, in any combination. The memory and other memories disclosed herein may be viewed as examples of what are more generally referred to as "processor-readable storage media" storing executable computer program code or other types of software programs. Articles of manufacture comprising such processor-readable storage media are considered embodiments of the invention. A given such article of manufacture may comprise, for example, a storage device such as a storage disk, a storage array or an integrated circuit containing memory. The processor may load the computer program code from the memory and execute the code to provide the functionalities of the host device 230.

The network interface provides circuitry enabling wireless communication between the host device 230, the sensing device 210 and the stimulating device 220.

FIG. 2A illustrates a modular physiologic monitoring system 200 that includes only a single instance of the sensing device 210 and the stimulating device 220 for clarity. It is to be appreciated, however, that modular physiologic monitoring system 200 may include multiple sensing devices and/or multiple stimulating devices. In addition, although FIG. 2A illustrates a modular physiologic monitoring system 200 in which the sensing device 210 and the stimulating device 220 are attached to the subject 201, embodiments are not limited to such arrangements. As described above, one or more sensing and/or stimulating devices may be part of contacting surfaces or non-contacting devices. In addition, the placement of sensing device 210 and stimulating device 220 on the subject 201 may vary as described above. Also, the host device 230 may be worn by the subject 201, such as being incorporated into a smartwatch or other wearable computing device. The functionality provided by host device 230 may also be provided, in some embodiments, by one or more of the sensing device 210 and the stimulating device 220. In some embodiments, as will be described in further detail below, the functionality of the host device 230 may be provided at least in part using cloud computing resources.

FIG. 2B shows a schematic diagram of aspects of the sensing device 210 in modular physiologic monitoring system 200. The sensing device 210 includes one or more of a processor, a memory device, a controller, a power supply, a power management and/or energy harvesting circuit, one or more peripherals, a clock, an antenna, a radio, a signal conditioning circuit, optical source(s), optical detector(s), a sensor communication circuit, vital sign sensor(s), and secondary sensor(s). The sensing device 210 is configured for wireless communication 225 with the stimulating device 220 and host device 230.

FIG. 2C shows a schematic diagram of aspects of the stimulating device 220 in modular physiologic monitoring system 200. The stimulating device 220 includes one or more of a processor, a memory device, a controller, a power supply, a power management and/or energy harvesting circuit, one or more peripherals, a clock, an antenna, a radio, a signal conditioning circuit, a driver, a stimulator, vital sign sensor(s), a sensor communication circuit, and secondary sensor(s). The stimulating device 220 is configured for wireless communication 225 with the sensing device 210 and host device 230.

Communication of data from the sensing devices and/or stimulating devices (e.g., patches and/or patch-module pairs) may be performed via a local personal communication device (PCD). Such communication in some embodiments takes place in two parts: (1) local communication between a patch and/or patch-module pair (e.g., via a hub or module of a patch-module pair) and the PCD; and (2) remote communication from the PCD to a back-end server, which may be part of a cloud computing platform and implemented using one or more virtual machines (VMs) and/or software containers. The PCD and back-end server may collectively provide functionality of the host device as described elsewhere herein.

As discussed above, there is a need to quickly convey information to a clinician, nurse, caregiver, administrator of a study, or other user in a manner that enables rapid interpretation of a data set. Often, in the context of human life, there are events and behaviors that happen throughout the day that may impact physiology or a disease state. Such events may have a relationship with a time of day, correspond to a particular event performed during the day, a sleep state, etc. One problem is that such data is often displayed in a format that does not reflect the cyclical nature of the data. Another problem is that while some data may be better displayed using a polar coordinate system, not all data benefits from this kind of display. Non-cyclical data, for example, may be easier to convey with a traditional Cartesian coordinate plot.

Yet another problem is that where a polar coordinate plot would be advantageous, the angular axis of that polar plot may not always be as simple as a day. Some metrics like sleep/wake cycle, physical activity level, and heart rate may be helpful to measure over a day, but other measurements are better displayed with a different time unit. For example, measurements and metrics associated with menstrual cycles, work-related insomnia, and seasonal affective disorder may be more suited for display with different time units.

Illustrative embodiments enable a clinician, nurse, caregiver, or administrator of a study to quickly visualize data in a way that is intuitive without having to plot the data multiple times in order to determine which data plot is optimal.

In various embodiments, data visualization methods are utilized for visualizing a chronological sequence of measurements from one or more patients or other subjects. The data visualization methods may include receiving measured data from a continuous monitoring process for one or more measured physiologic parameters, determining an optimal way of generating a visualization of the measured data (e.g., an optimal type of plot for displaying the measured data, such as selecting between use of a polar coordinate plot and a Cartesian coordinate plot), automatically transforming the measured data into presented measured data using the determined optimal way of generating the visualization, and presenting or otherwise outputting the presented measured data on a display.

Figure 3:
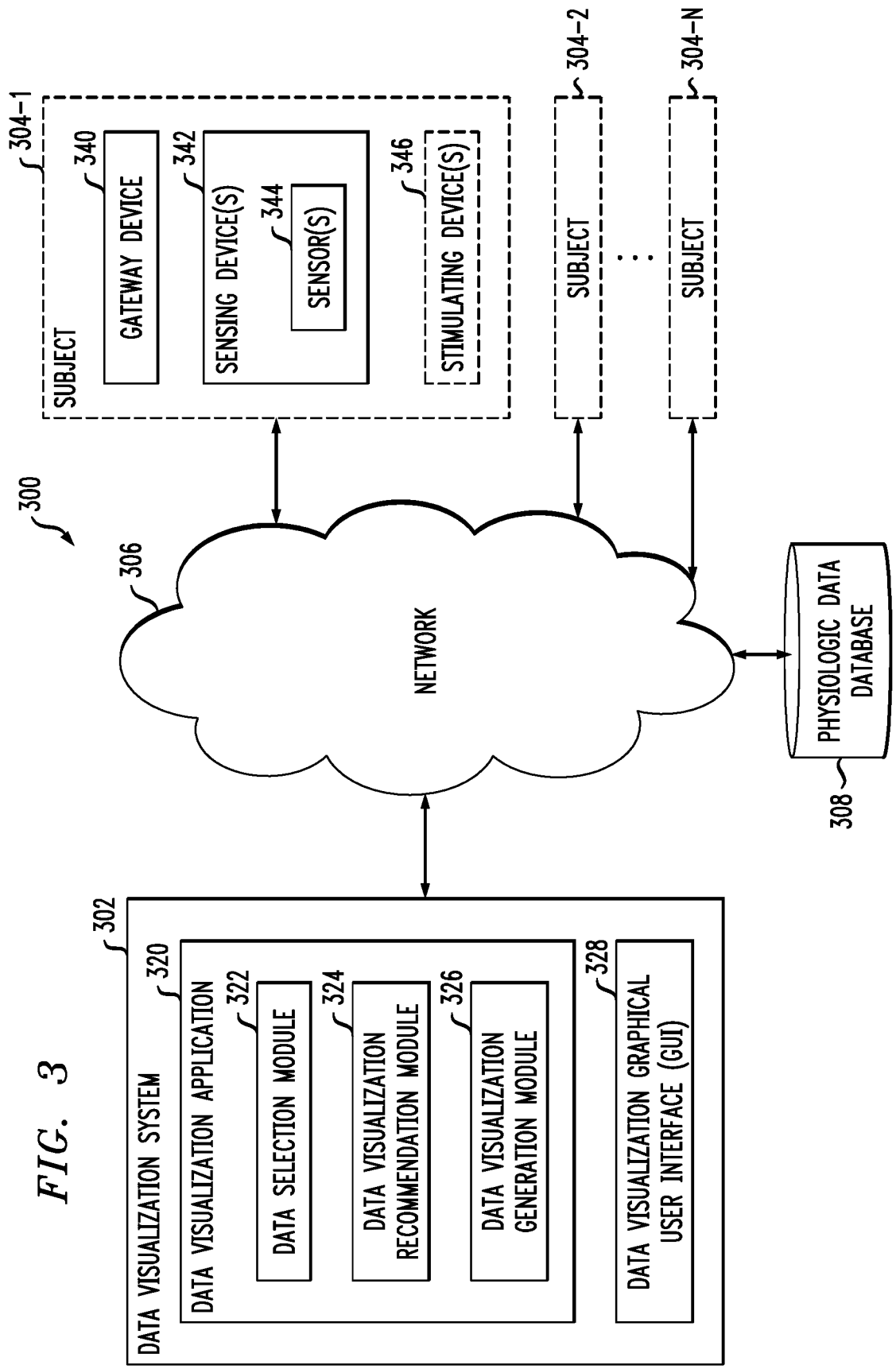
FIG. 3 illustrates a data visualization system, according to an embodiment of the invention.

FIG. 3 shows a modular physiologic monitoring system 300, which includes a data visualization system 302 and subjects 304-1, 304-2, ... 304-N (collectively, subjects 304). The data visualization system 302 implements a data visualization application 320, and is configured to communicate over network 306 with devices associated with the subjects 304. For example, FIG. 3 shows subject 304-1 associated with a gateway device 340, one or more sensing devices 342 comprising one or more sensors 344, and optionally one or more stimulating devices 346. Although not shown, other ones of the subjects 304-2 through 304-N are assumed to similarly be associated with a gateway device, one or more sensing devices, and optionally one or more stimulating devices. In some embodiments, the gateway device 340, the one or more sensing devices 342, and the one or more stimulating devices 346 are implemented using patch-module pairs as described above. In other embodiments, however, the gateway device 340, the one or more sensing devices 342, and the one or more stimulating devices 346 may utilize various other form factors. The data visualization system 302, in some embodiments, is implemented as part of a host device as described above.

The data visualization application 320 can be installed or run on one or more physical or virtual computing resources. Physical computing resources include, but are not limited to, a smartphone, laptop, tablet, desktop, wearable computing device, server, etc. Virtual computing resources include, but are not limited to, VMs, software containers, etc. The data visualization application 320 is configured to store, analyze and display physiological data from one or more of the subjects 304 utilizing a data selection module 322, a data visualization recommendation module 324, and a data visualization generation module 326.

The data selection module 322 enables a user of the data visualization application 320 to select what data to visualize. For example, the user of the data visualization application 320 may utilize the data selection module 322 to select a particular patient (e.g., one of the subjects 304), a particular time period, a particular type or types of physiologic measurements or parameters, etc.

The data visualization recommendation module 324 is configured to analyze the selected data to determine how the selected data should be visualized. In some embodiments, this includes the data visualization recommendation module 324 recommending a particular data plot type (e.g., one of a polar coordinate plot and a Cartesian coordinate plot) and enabling a user to accept or reject the recommendation. In some embodiments, the data visualization recommendation module 324 automatically selects the plot type without requiring user input or confirmation of the plot type recommendation.

The data visualization generation module 326 is configured to pull the selected data and plot the selected data using the recommended plot type (which, as noted above, may be selected by the user or selected automatically). The selected data may be obtained from a physiologic data database 308 coupled to the network 306, or directly from devices associated with one or more of the subjects 304. For example, assume that the selected data includes physiologic data associated with subject 304-1. In this example, the selected data may be obtained from the gateway device 340 associated with the subject 304-1. The gateway device 340 may alternatively stream or otherwise store data for the subject 304-1 in the physiologic data database 308. In such cases, the selected data may be obtained from the physiologic data database 308. In still other embodiments, the selected data may be obtained at least in part from the gateway device 340 and the physiologic data database 308 (e.g., such as where most recent data is obtained from the gateway device 340, while older data is obtained from the physiologic data database 308). Various other examples are possible, such as where the selected data is obtained directly from one or more of the sensing devices 342.

In FIG. 3, the physiologic data database 308 is shown as being implemented external to the data visualization system 302 and data visualization application 320. It should be appreciated, however, that in other embodiments the physiologic data database 308 may be implemented at least in part internal to the data visualization system 302 and/or data visualization application 320. The data stored in the physiologic data database 308 may vary based on the types of information collected from the subjects 304. In some embodiments, the data is assumed to include data associated with various physiologic parameters such as heart rhythm, heart rate, QRS duration, PR interval, QT interval, RR variability, ST segments, hemoglobin saturation, physical activity, posture position, respiration, sleep parameters, etc.

The data visualization system 302 also implements a data visualization graphical user interface (GUI) 328, which is configured to display data visualizations generated by the data visualization generation module 326 of the data visualization application 320. The data visualization GUI 328 is also configured to allow a user to interact with data in the generated data visualizations (e.g., adding day/night indicators or other filters or overlays, expanding sections of the generated data visualizations, overlaying different physiologic metrics, etc.).

In some embodiments, the subject 304-1 is assumed to be a human patient. The gateway device 340 transmits data from the one or more sensing devices 342 to the data visualization application 320 (or to the physiologic data database 308 for storage therein) over network 306. The one or more sensing devices 342 comprise one or more sensors 344 which send data to the gateway device 340 (e.g., using ultra-low power wireless communication in some embodiments). The one or more sensors 344 are configured to detect and measure various physiologic parameters, and may include various types of sensors. Sensor types include, but are not limited to, motion sensors, temperature sensors, humidity sensors, cameras, microphones, radiofrequency receivers, thermal imagers, radar devices, lidar devices, ultrasound devices, speakers, EEG electrodes, EKG electrodes, heart rate sensors, etc.

The network 306 may comprise a physical connection (wired or wireless), the Internet, a cloud communication network, etc. Examples of wireless communication networks that may be utilized include networks that utilize Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques known in the art. In some embodiments, the communication network may allow ubiquitous access to shared pools of configurable system resources and higher-level services that can be rapidly provisioned with minimal management effort, often over the Internet and relies on sharing of resources to achieve coherence and economies of scale, like a public utility, while third-party clouds enable organizations to focus on their core businesses instead of expending resources on computer infrastructure and maintenance.

Figure 4:
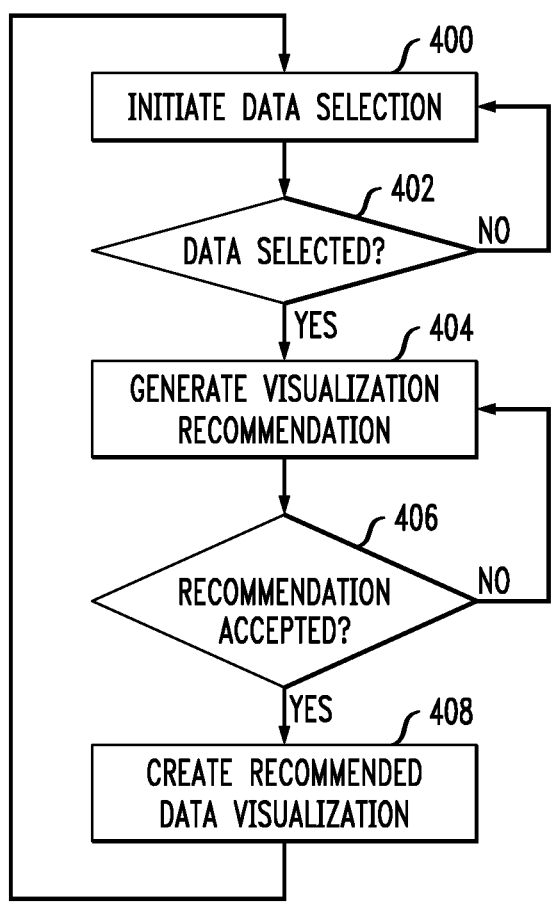
FIG. 4 illustrates a process flow for creating data visualizations utilizing the FIG. 3 data visualization system, according to an embodiment of the invention.

FIG. 4 illustrates a process flow for creating data visualizations utilizing the data visualization application 320. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The FIG. 4 process flow begins in step 400 with initiating data selection utilizing the data selection module 322 of the data visualization application 320. In step 402, a determination is made as to whether data has been selected. If the result of the step 402 determination is yes, and if the selected data is valid, the data visualization application 320 generates a visualization recommendation in step 404 utilizing the data visualization recommendation module 324. If the result of the step 402 determination is no, processing may return to step 400 (e.g., until the user has selected valid data, or until the flow exits or times out). In step 406, a determination is made as to whether the recommended data visualization is accepted by the user. If the result of the step 406 determination is yes, the data visualization application 320 creates the recommended data visualization in step 408 utilizing the data visualization generation module 326. If the result of the step 406 determination is no, the data visualization application 320 will return to step 404 (e.g., until the recommended data visualization is accepted by the user, or until the flow exits or times out).

Figure 5:
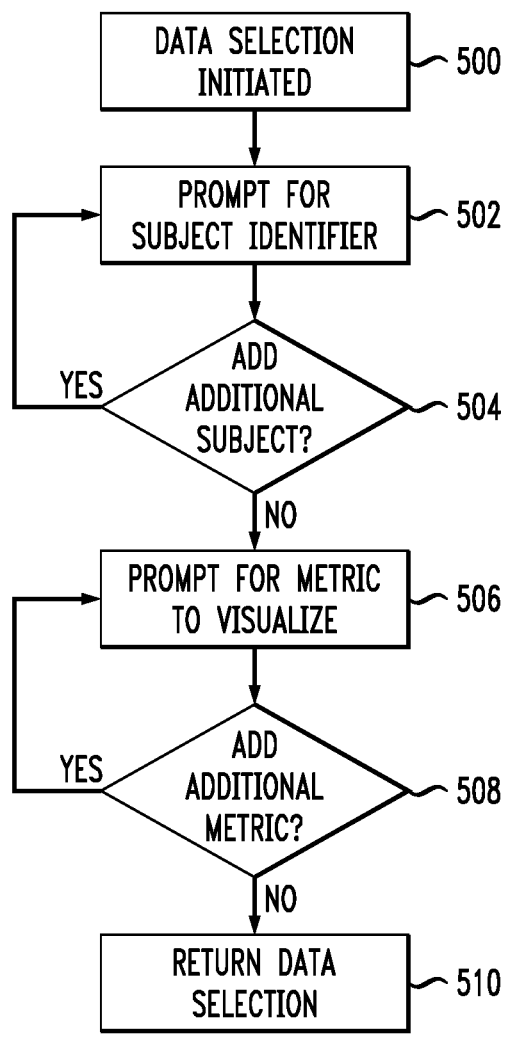
FIG. 5 illustrates a process flow for selecting data to be visualized utilizing the FIG. 3 data visualization system, according to an embodiment of the invention.

FIG. 5 illustrates a process flow for selecting data to be used in creating one or more data visualizations utilizing the data selection module 322 of the data visualization application 320. The FIG. 5 process flow begins in step 500 with initiating data selection. In step 502, a user is prompted to select one or more patient or subject identifiers (e.g., whose associated data is to be visualized). The patient or subject identifiers or IDs may comprise a name, number or other identifying data. In some embodiments, the user enters the patient or subject IDs automatically, such as by scanning a quick response (QR) code (e.g., which may be on a hospital band worn by a patient or subject). The user may also select from a list of available patient or subject IDs pulled from the physiologic data database 308. In step 504, a determination is made as to whether to add additional patients or subjects. If the result of the step 504 determination is yes, processing returns to step 502. If the result of the step 504 determination is no, processing proceeds to step 506 where the user is prompted to select particular physiologic metrics to be visualized. Examples of physiologic metrics that may be selected include heart rhythm, heart rate, QRS duration, PR interval, QT interval, RR variability, ST segments, hemoglobin saturation, physical activity, posture position, respiration, sleep parameters, etc. In some embodiments, the user selects from a list of available physiologic metrics that are pulled from the physiologic data database 308. In other embodiments, the user may also or alternatively select a visualization profile or template (e.g., comprising a set of physiologic parameters useful for monitoring certain conditions, such as a heart health profile, a sleep profile, etc.). Such templates may also be pulled from the physiologic data database 308. In step 508, a determination is made as to whether to add additional physiologic metrics for the data visualization. If the result of the step 508 determination is yes, processing returns to step 506. If the result of the step 508 determination is no, processing proceeds to step 510 where the data selections are returned to the data visualization application 320.

Figure 6:
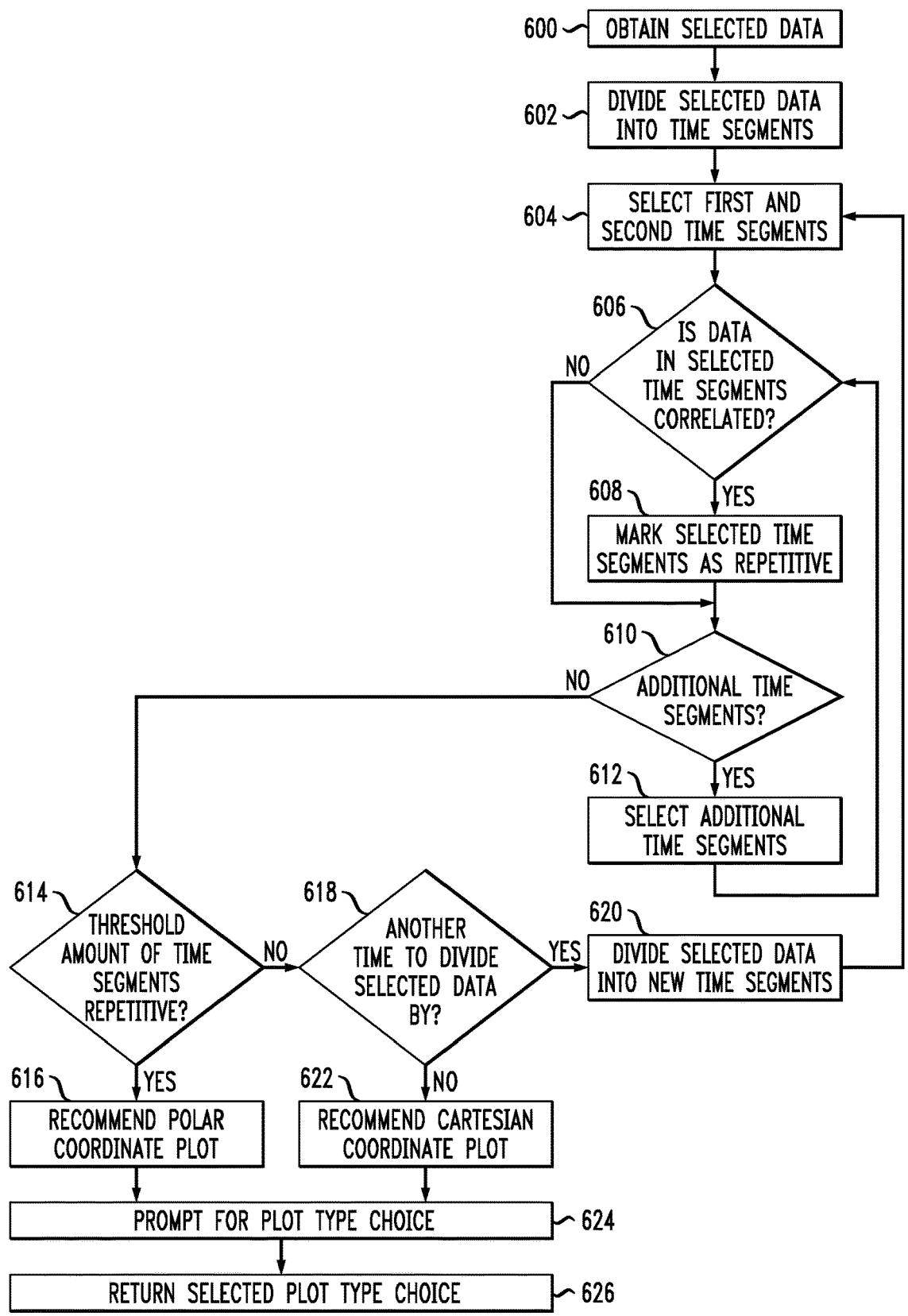
FIG. 6 illustrates a process flow for selecting a type of data visualization to be created utilizing the FIG. 3 data visualization system, according to an embodiment of the invention.

FIG. 6 illustrates a process flow for selecting a type of data visualization to create utilizing the data visualization recommendation module 324 of the data visualization application 320. The FIG. 6 process flow begins with obtaining the selected data (e.g., as selected using the FIG. 5 process flow) in step 600. The selected data may be obtained from the physiologic data database 308, from gateway devices associated with the subjects 304 (e.g., gateway device 340 associated with subject 304-1), etc. In step 602, the selected data is divided into time segments (e.g., equal time segments). In some embodiments, step 602 includes dividing the data into a smallest time segment size that is supported by the data visualization application 320. The supported time segment sizes may be based on common time units (e.g., one or more seconds, minutes, hours, days, weeks, months, years, etc.). In some cases, every multiple of the common time units is an option or supported time segment (e.g., one second, two seconds, . . . , one hour, two hours, . . . , etc.). The supported time segment sizes, in some embodiments, are narrowed down based on the physiologic metrics that are to be visualized. Physical activity level or sleep pattern physiologic parameters, for example, may start with a time segment size of one day, while menstrual cycle physiologic parameters may start with a time segment size of 28 days, etc. In some cases, the supported time segment sizes may be based on how frequently the physiologic metrics to be visualized are obtained (e.g., if a particular physiologic metric is obtained only once an hour, the starting time segment size should be at least one hour). In some embodiments, a user is able to override or change the time segment size utilizing the data visualization GUI 328 (e.g., including after a data visualization is created and presented, whereby responsive to user changes in the time segment size the presented data visualization may be dynamically updated).

In step 604, first and second time segments are selected. The first and second time segments may be the time segments obtained from step 602 that come first and second in time, respectively. In step 606, a determination is made as to whether the data in the selected first and second time segments are correlated. Step 606 may use various techniques for determining whether data in the selected first and second time segments are correlated including, but not limited to: analysis of variance (ANOVA); coherence analysis; bicoherence analysis; state segmentation of the data; etc. State segmentation of the data may include comparison of timestamps within a day, comparison of a selective criteria on a recorded metric, such as motion (e.g., low, moderate, high), posture (e.g., sitting, standing, laying down, etc.), respiration (e.g., inhaled, exhaled, etc.), repetitive/non-repetitive movements, etc. In some embodiments, step 606 utilizes a correlation threshold such as a correlation coefficient (e.g., 95%). If the result of the step 606 determination is yes, processing proceeds to step 608 where the selected first and second time segments are marked as repetitive. It should be noted that step 608 includes marking two time segments as repetitive with respect to one another, meaning that one time segment may be marked repetitive multiple times. The first time segment, for example, may be marked as repetitive with the second time segment and at least one additional time segment, where the additional time segment does not necessarily follow the second time segment in time (e.g., the first time segment may be marked as repetitive with the second time segment and a fourth time segment, but not with a third time segment). Following step 608, or if the result of the step 606 determination is no, processing proceeds to step 610.

In step 610, a determination is made as to whether there are more time segments to compare. If the result of the step 610 determination is yes, processing proceeds to step 612 where additional time segments that have not yet been compared are selected and processing then returns to step 606. For example, if first and second time segments have been compared but first and third time segments have not been compared, step 610 results in yes and the first and third time segments are selected in step 612. If the result of the step 610 determination is no, or if step 610 has already been run some designated threshold number of iterations (e.g., where the designated threshold may be set based on available computing resources, as a percentage of a total possible combinations of the time segments, etc.), processing proceeds to step 614.

In step 614, a determination is made as to whether a threshold amount of the time segments have been marked as repetitive (e.g., determine if a significant amount of the time segments are repetitive or redundant with respect to one another). The threshold may be set by default, by a user, or automatically based on the number of time segments. For example, the threshold may be set to 50%. In some embodiments, the amount of redundancy or repetitiveness is determined by dividing the total number of repetitive time segments by the total number of time segments (e.g., if there are three time segments and two of the three are repetitive, then 66% of the time segments are repetitive meeting the 50% threshold). In other embodiments, the amount of redundancy or repetitiveness is determined by dividing the total number of redundant time segment combinations by the total number of possible time segment combinations (or the total number of time segment combinations compared in step 606). For example, if there are three time segments, and if the first and second time segments are repetitive with respect to one another but the third time segment is not repetitive with respect to either the first or second time segment, then out of three combinations (e.g., first and second, first and third, second and third) only ⅓ or 33% of the total possible time segment combinations are repetitive with respect to one another and the 50% threshold is not met. Various other techniques for determining whether a significant amount of the time segments are repetitive may be used (e.g., such as determining that there is a threshold number of repetitive time segments without comparing to a total number of time segments or total number of possible time segment combinations). In addition, various other significance thresholds (e.g., thresholds other than 50%) may be used.

If the result of the step 614 determination is yes, processing proceeds to step 616 where a polar coordinate plot is recommended for the data visualization. For the polar coordinate plot, the time segment size utilized in step 602 (or step 620 described below) is set equal to 360 degrees. For example, if the time segment size is one day, then the polar coordinate plot may have midnight at 0 degrees, 6:00 AM at 90 degrees, noon at 180 degrees, and 6:00 PM at 270 degrees. If the result of the step 614 determination is no, processing proceeds to step 618.

In step 618, a determination is made as to whether there is another time unit or time segment size that the selected data may be divided by. As noted above, in some embodiments step 602 divides the selected data into the smallest possible or supported time segment size. In such embodiments, step 618 may include determining whether there is a larger possible or supported time segment size to divide the selected data by. For example, if the time segment size utilized in step 602 is one day, step 618 may determine whether there is a larger supported time segment size (e.g., two days, one week, etc.). If the result of the step 618 determination is yes, processing proceeds to step 620 where the selected data is divided into new time segments using a time segment size different than that utilized in step 602. The FIG. 6 process flow then returns to step 606 to compare the new time segments to one another for repetitiveness or redundancy.

If the result of the step 618 determination is no, processing proceeds to step 622 where a Cartesian coordinate plot is recommended. In some embodiments, the step 618 determination is no when there are no time segment sizes left to divide the data by and there is an insignificant amount of repetitive time segments with all the different time segment sizes that have been compared in multiple iterations of running through steps 606 through 614. Following steps 616 and 622, a user may be prompted for a plot type choice in step 624. This allows the user to override the recommendation from step 616 or step 624 if so desired. For example, the FIG. 6 process flow may iterate through until a polar coordinate plot is chosen for a relatively large time segment size (e.g., one month) and the user may determine that this time segment size is not useful for a particular task and thus the user may override the polar coordinate plot recommendation and choose a Cartesian coordinate plot. The user may also override the Cartesian coordinate plot recommendation if desired. The selected plot type choice is returned to the data visualization application 320 in step 626. In some embodiments, step 624 is skipped or omitted and the FIG. 6 process flow simply returns the recommended plot type (e.g., from step 616 or step 622) in step 626.

In some embodiments, if there are two or more additional possible time segment sizes to divide by (e.g., the time segment size utilized in step 602 or a previous iteration of step 620 is one day, and additional supported time segment sizes of two days and one week have not been tested), the next smallest supported time segment size is selected and utilized in step 620 (e.g., two days is selected rather than one week). By selecting the next smallest supported time segment size (rather than a next supported time segment size at random), the FIG. 6 process flow can determine or capture the smallest supported time segment size or time unit at which the selected data has a repeating pattern. This is also the reason that some embodiments select the smallest supported time segment size (e.g., one day) in step 602, because if the selected data is repetitive on the smallest supported time segment size (e.g., one day) the selected data may also be likely to repetitive on larger supported time segment sizes (e.g., every two days, week to week, month to month, etc.).

It should be appreciated, however, that in other embodiments it may be desired to start in step 602 with the largest supported time segment size. In such embodiments, the logic of step 614 may be reversed such that if the threshold amount of time segment sizes are repetitive the flow proceeds to step 618 to determine whether there is a smaller time segment size to divide by and iterations of step 620 select smaller and smaller time segment sizes until the step 614 determination results in no. In such cases, the FIG. 6 process flow may then proceed to step 616 where a polar coordinate plot is recommended for any of the time segment sizes that have previously been compared and determined to be repetitive such that the data visualization GUI 328 may present such different options to the user for dynamically updating the presented data visualization. The FIG. 6 process flow may also be modified such that the step 614 determination follows the "no" branch of the step 618 determination, such that the FIG. 6 process flow tests all supported time segment sizes. The step 614 determination in such cases would then be used to determine whether each of the supported time segment sizes is more suitable to a polar coordinate plot visualization or a Cartesian coordinate plot visualization. Thus, the data visualization GUI 328 may dynamically switch between polar coordinate plots and Cartesian coordinate plots as the user adjusts the time segment size to be viewed.

FIG. 7 illustrates a process flow for creating a data visualization utilizing the data visualization generation module 326 of the data visualization application 320. In step 700, generation of a data visualization is initiated. In step 702, data selection choices are obtained (e.g., from the data selection module 322 utilizing the FIG. 5 process flow). In step 704, a plot type selection choice is obtained (e.g., from the data visualization recommendation module 324 utilizing the FIG. 6 process flow). In step 706, the selected data is obtained (e.g., from physiologic data database 308, from gateway devices associated with one or more of the subjects 304, etc.). The selected data obtained in step 706 is then plotted according to the selected plot type in step 708. Plotting the data may include assigning a variable or physiologic metric to each axis, comparing two or more physiologic metrics to one another (e.g., comparing a first physiologic metric to a second physiologic metric, comparing first and second physiologic metrics to a third physiologic metric, etc.). In some embodiments, one or more physiologic metrics are compared to a time variable. Multiple plots (e.g., of two or more physiologic metrics with respect to a time variable) may be overlaid as described in further detail below. The plotted data is then output in step 710 to the data visualization GUI 328.

FIG. 8 shows a table of physiologic metrics that may be stored in the physiologic data database 308. The table 800 more particularly includes columns for a patient or subject ID, date and time, and physiologic metrics such as heart rate (HR) in beats per minute (bpm), blood pressure (BP) in millimeters of Mercury (mmHg), SpO2 percentage, respiratory rate in bpm and QRS duration in milliseconds (ms). The table 800 may be viewed more particularly as an example of selected data to be used in creating a data visualization, where in the case of table 800 the patient ID of 3965786 was selected along with a particular time frame (e.g., 11/21/19 between 11:46:28 and 11:46:36) and the physiologic parameters of HR, BP, SpO2, respiratory rate and QRS duration. Thus, the table 800 may represent a subset of the data that is stored in the physiologic data database 308 (or obtained from a gateway device associated with a given subject having the 3965786 patient ID). Various other physiologic metrics may be captured and stored, including but not limited to heart rhythm, heart rate, QRS duration, PR interval, QT interval, RR variability, ST segments, hemoglobin saturation, physical activity, posture position, respiration, sleep parameters, etc.

Figure 9A:
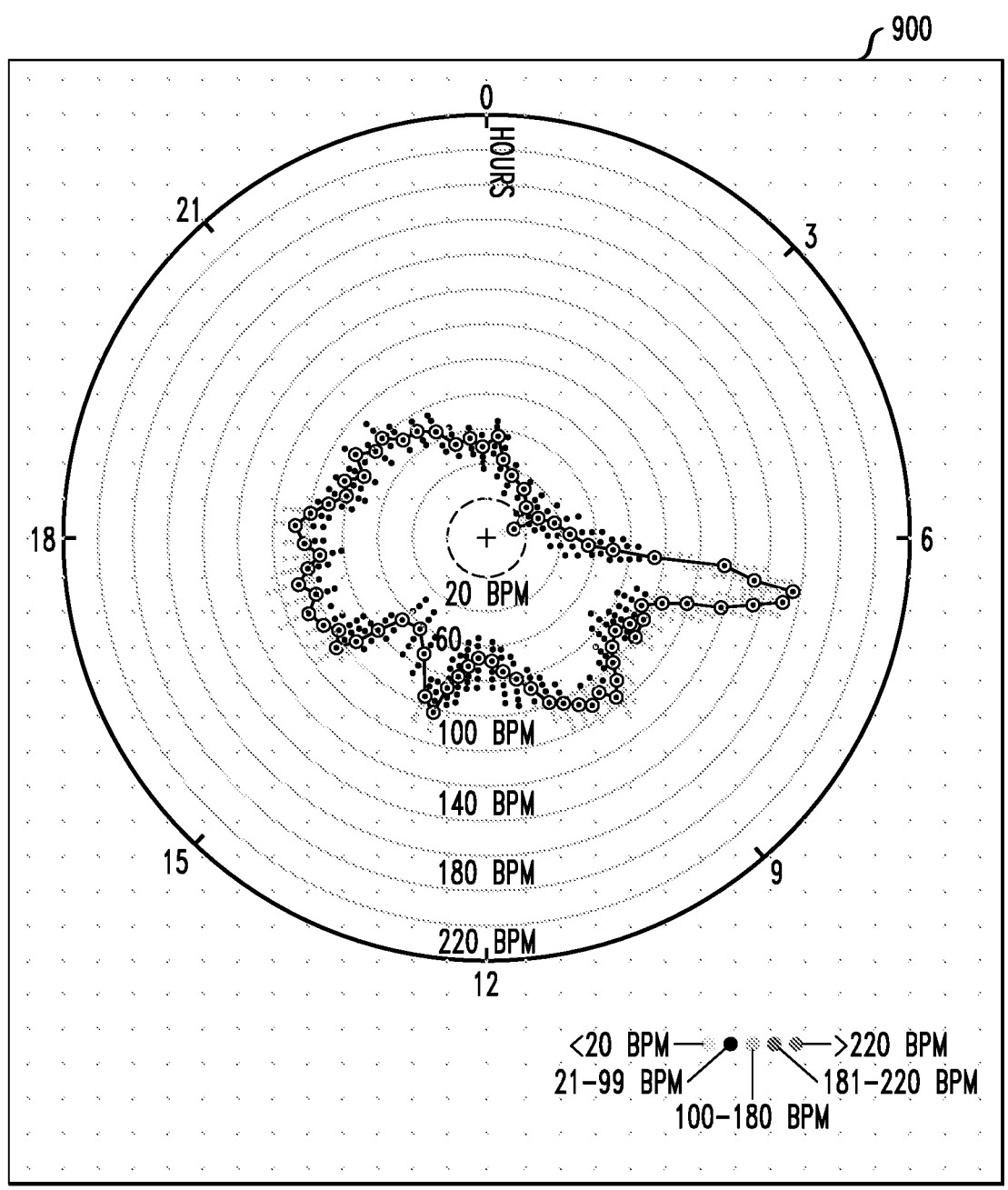
FIGS. 9A and 9B illustrate data visualizations presented using the data visualization graphical user interface of the FIG. 3 data visualization system, according to an embodiment of the invention.
Figure 9B:
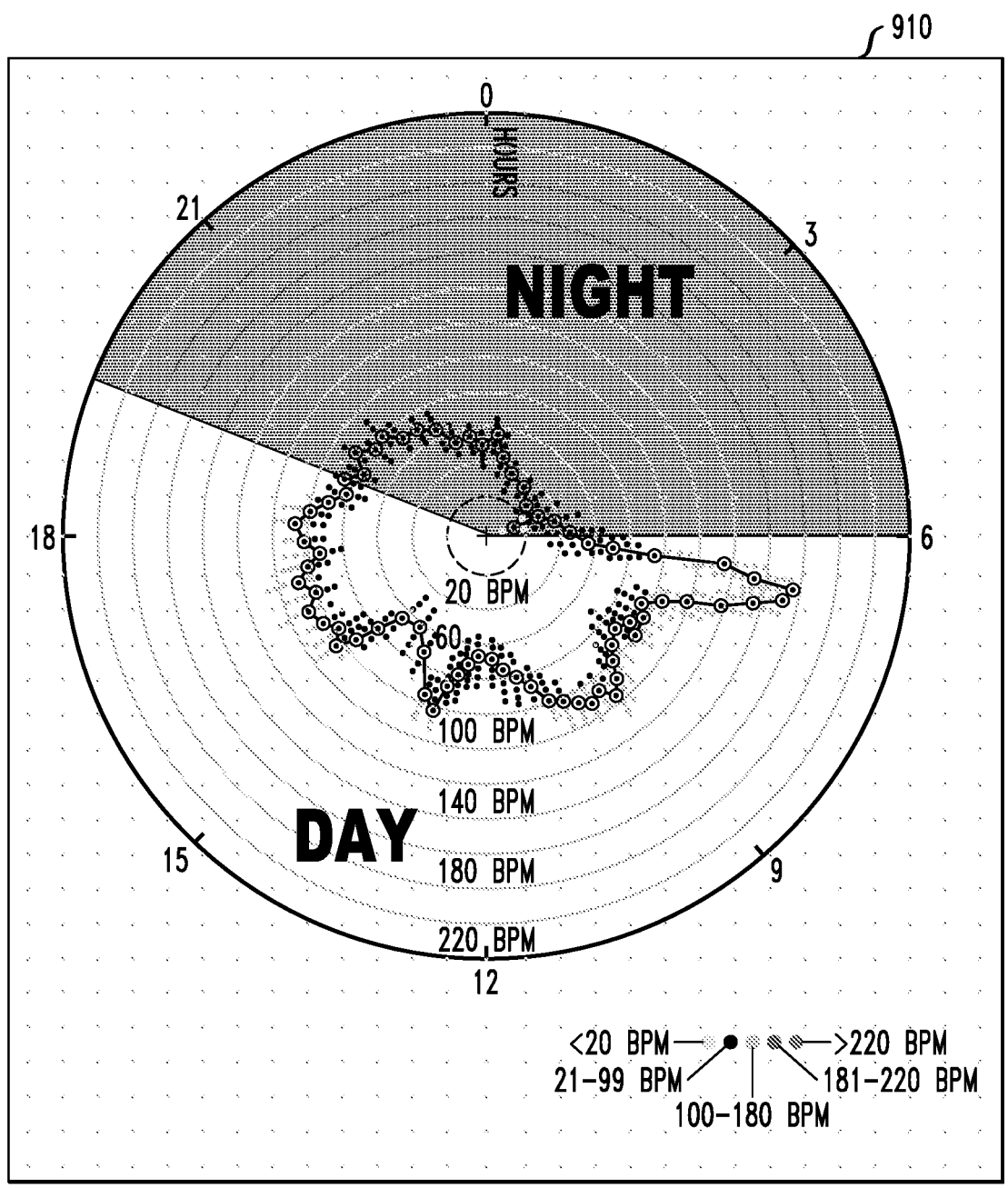

Various examples of data visualizations which may be generated using the data visualization application 320 of data visualization system 302 will now be described with respect to FIGS. 9A-9B, 10A-10B, 11A-11H and 12A-12D. The data visualization GUI 328 of the data visualization system 302 may be used to control various aspects of such data visualizations. Generally, the data visualization GUI 328 will display the plot of the selected data that is produced and output by the data visualization generation module 326 of the data visualization application 320. FIG. 9A shows a visualization 900 of a polar coordinate plot of a patient's average heart rate over the course of each day. FIG. 9B shows a visualization 910, which is similar to the visualization 900 but includes a day/night filter overlaid on the polar coordinate plot to better orient the user and better align the patient's heart rate with their normal daily activities (e.g., awake or asleep). The individual data points in the polar coordinate plots of visualizations 900 and 910 may be shaded or color coded to correspond to different ranges of the patient's heart rate, such as using different shading or color for heart rates: below 20 bpm; between 21-99 bpm; between 100-180 bpm; between 181-220 bpm; and greater than 220 bpm. It should be appreciated that these ranges are selected by way of example, and that other ranges (including more or fewer ranges) may be used in other embodiments. Further, these ranges may have data points that are different shapes (e.g., circles, triangles, crosses, etc.) rather than or in addition to different shading or different coloring. The data visualizations 900 and 910 of FIGS. 9A and 9B, as well as other data visualizations described herein, may be used to facilitate rapid assessment of datasets collected from a patient or other subject. An observer or user is able to utilize the data visualizations to quickly assess changes in the data, and to navigate through the data to hone in on a problem or event and make an assessment about the physiologic or disease state of the subject.

The data visualizations may be utilized to provide a periodic view (e.g., daily as in data visualizations 900 and 910, weekly, monthly, etc.) of one or more measured physiologic metrics. Contextual overlays may be quickly superimposed above the data set (e.g., such as the day/night filter overlay shown in data visualization 910) to visually assess cause and effect. Such contextual information may include day/night, posture, postural changes, activity level, time at a particular posture, a period of snoring, an event such as taking of a pill, an annotation, etc. The annotation may be related to various factors, such as a symptom, consumption of a meal, a location (e.g., work, home, commute, etc.), conversation, proximity to any person, proximity to a particular person or persons, computer usage, etc.

The view structure of various data visualizations allows an observer to utilize interface features of the data visualization GUI 328 to quickly visualize key metrics and contextually related events in such a way as to determine how various daily or behavioral activities may affect the physiologic state of the subject. In addition, the data visualization GUI 328 provides interface features that enable a user to navigate from several days down to a single day, an hour, a minute, etc. so as to visualize a particular event. The data visualization GUI 328 may include or display a linear rhythm strip (e.g., as described in further detail below with respect to FIG. 13C) below the plot (e.g., a polar coordinate plot), where the linear rhythm strip is auto-scaled to the same scale as the display (e.g., of the polar coordinate plot) such that the observer can quickly visualize both the polar and linear display during an analysis. Further, the observer can quickly zoom, pan, rotate, etc. through the data so as to hone in on a particular event and analyze it in detail.

In some embodiments, the data visualization GUI 328 includes interface features for selecting various contextual events to overlay or display in conjunction with a displayed plot. Such contextual events include a size, overlaying additional event types and/or additional physiologic metrics into the plotted data, such that various events or physiologic metrics may be simultaneously visualized. As an example, the plot visualization output by the data visualization generation module 326 for display using the data visualization GUI 328 may initially include a plot of heart rate such as in data visualizations 900 and 910 of FIGS. 9A and 9B. A user may "zoom in" to a particular time range where the heart rate data is to be further analyzed, and the user may then utilize interface features of the data visualization GUI 328 to overlay or display additional physiologic metrics (e.g., respiratory rate, posture, etc.) to determine if the heart rate data (e.g., elevated heart rate) correlates as expected with such additional physiologic metrics.

The data visualizations 900 and 910 of FIGS. 9A and 9B display heart rate on a 24-hour clock using polar coordinate plots, where the data visualization 910 includes the day/night overlay. The day/night overlay allows the observer to quickly see where in the day and under what conditions the heart rate of the subject is changing. As noted above, various other overlays or contextual events may also be used, such as overlaying a filter showing when the subject was awake/asleep, moving/stationary, etc. In some embodiments, two or more overlays or filters are used simultaneously.

Figure 10A:
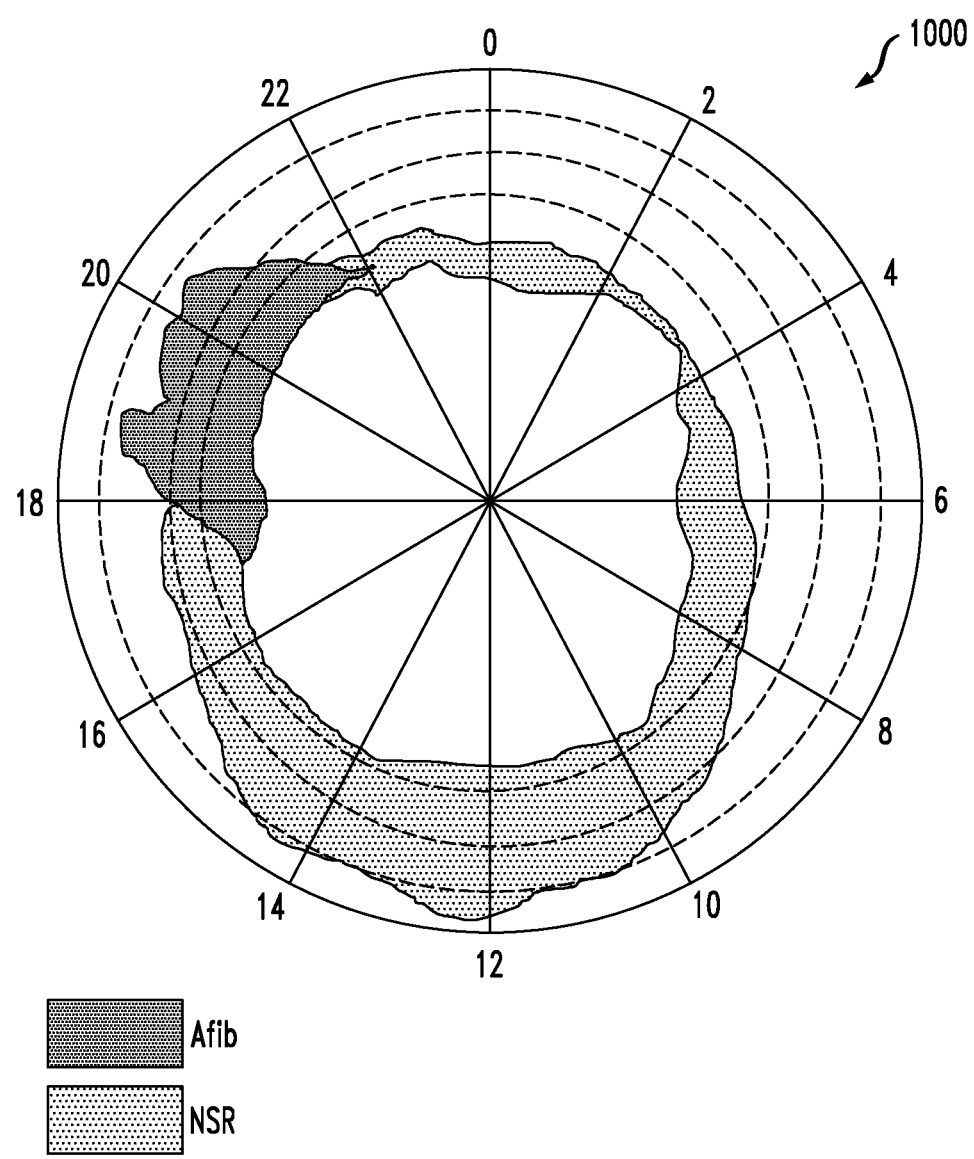
FIGS. 10A and 10B illustrate additional data visualizations presented using the data visualization graphical user interface of the FIG. 3 data visualization system, according to an embodiment of the invention.
Figure 10B:
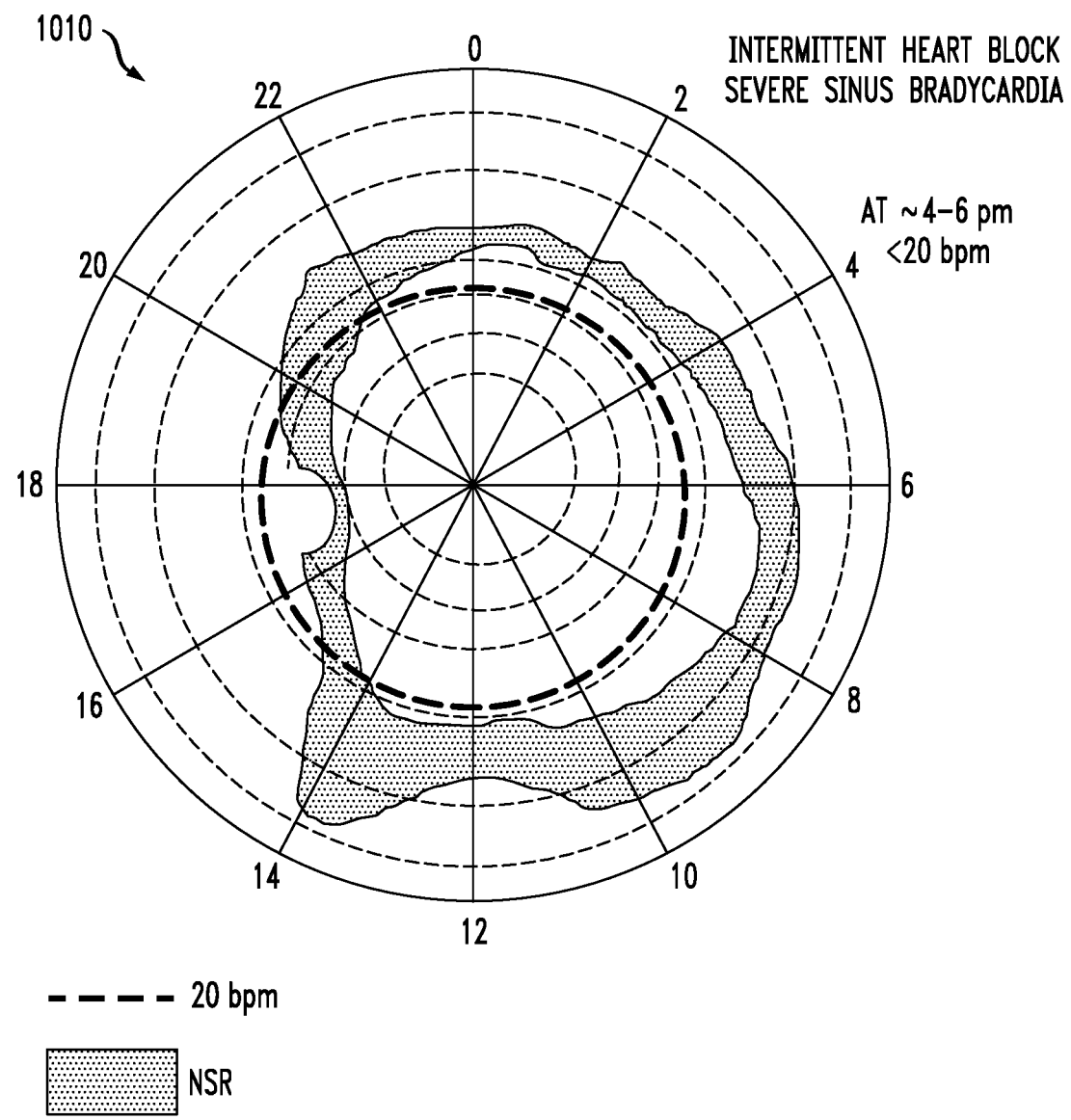

FIGS. 10A and 10B show polar coordinate plot data visualizations 1000 and 1010, respectively, where a subject's heart rate is plotted. The data visualization 1000 shows the data highlighted in different colors or shading representing certain conditions, specifically normal sinus rhythm (NSR) and atrial fibrillation (Afib). The data visualization 1010 shows the data plotted with NSR highlighted in one color, along with an overlay dashed line corresponding to a specific heart rate of 20 bpm. This filter or overlay in the data visualization 1010 may be useful for quick visualization of conditions such as intermittent heart block or severe sinus bradycardia. In the data visualization 1010, for example, such conditions are present between approximately 4:00 PM-6:00 PM for the subject.

FIGS. 11A-11H show respective polar coordinate plot data visualizations 1100, 1110, 1120, 1130, 1140, 1150, 1160 and 1170 (labeled as 1 through 8), illustrating various different cardiac conditions.

Figure 11A:
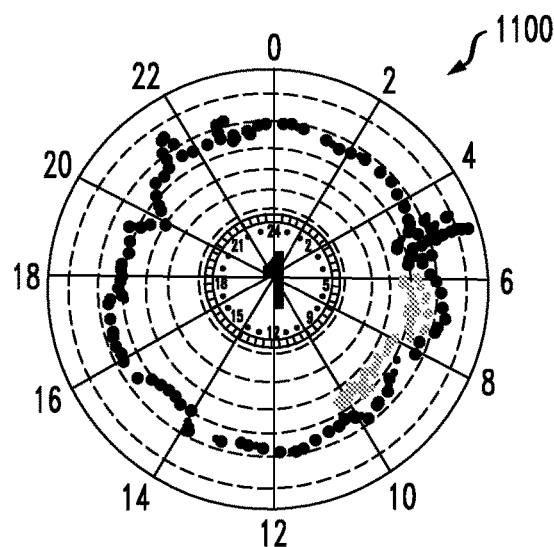
FIGS. 11A-11H illustrate additional data visualizations presented using the data visualization graphical user interface of the FIG. 3 data visualization system, according to an embodiment of the invention.

Data visualization 1100 in FIG. 11A plots heart rate and regions of high activity levels associated with waking up and getting out of bed in the morning, the plot illustrates occurrence of atrial fibrillation between the hours of 4-6 am just before the subject awakens.

Figure 11B:
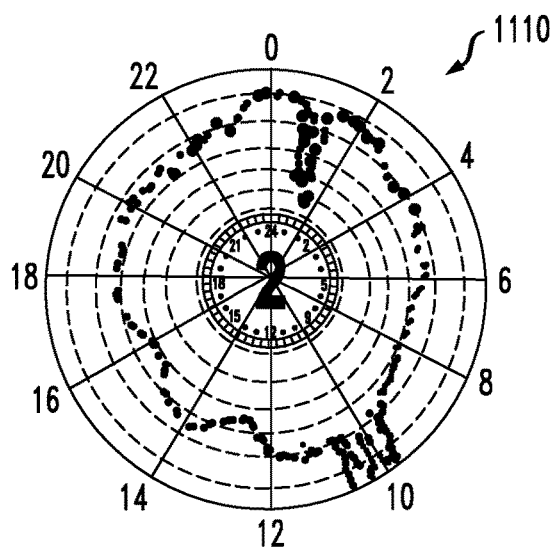

Data visualization 1110 in FIG. 11B plots heart rate and illustrates sudden changes in heart rate, with heart rate dropping at about 1am, perhaps due to pause or other serious condition, and also illustrates a sudden increase at 10 am, perhaps due to atrial fibrillation, sudden heavy activity, or the like.

Figure 11C:
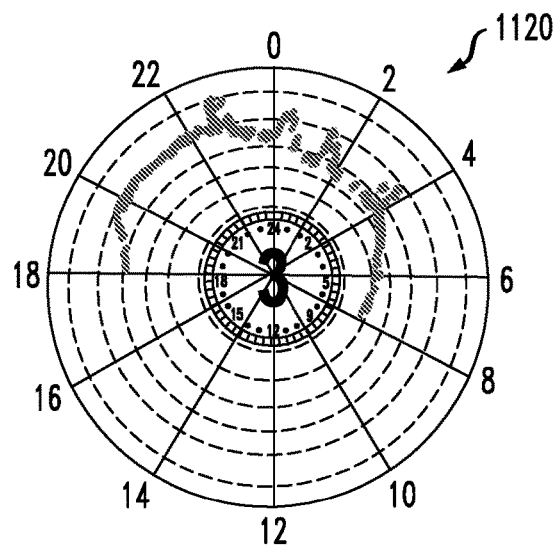

Data visualization 1120 in FIG. 11C plots QT interval. QT interval is calculated as the time from the start of the Q wave to the end of the T wave from the EKG of a subject, and approximates to the time taken from when the cardiac ventricles start to contract to when they finish relaxing. An abnormally long or abnormally short QT interval is associated with an increased risk of developing abnormal heart rhythms and sudden cardiac death. The plot 1120 of FIG. 11C shows QT interval over time for a subject and illustrates a change in QT interval after 6:00 pm correlating to a change caused by a medication, as well as erratic and dangerous changes in QT interval throughout the night returning to a lower value in the morning as the medication wears off.

Figure 11D:
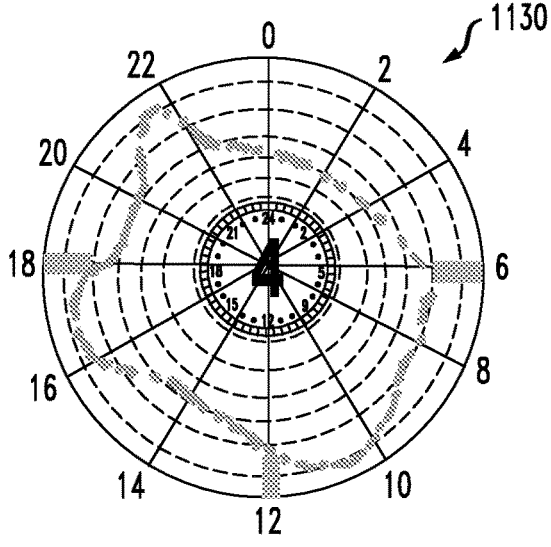

Data visualization 1130 in FIG. 11D plots QT interval (e.g., a time from the start of the Q wave to the end of the T wave in an EKG) physiologic metrics, and is annotated with times at which medications are administered (e.g., at 6:00 am, 12:00 pm, 6:00 pm), illustrating cardiac conditions related to certain heart rhythm arrythmias.

Figure 11E:
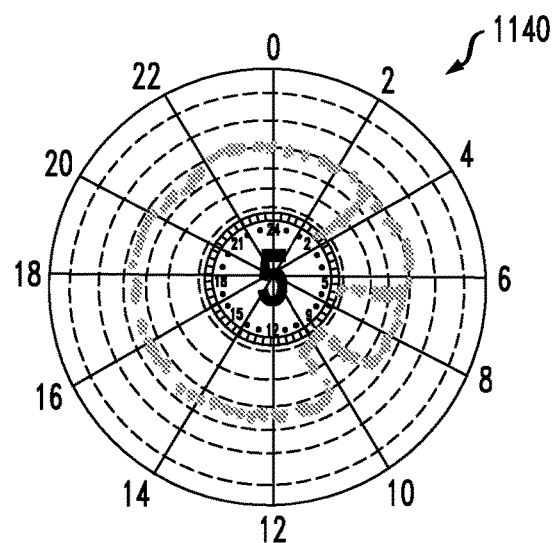

Data visualization 1140 in FIG. 11E plots heart block physiologic metrics including a median filtered heart rate, illustrating cardiac conditions relative to heart block.

Figure 11F:
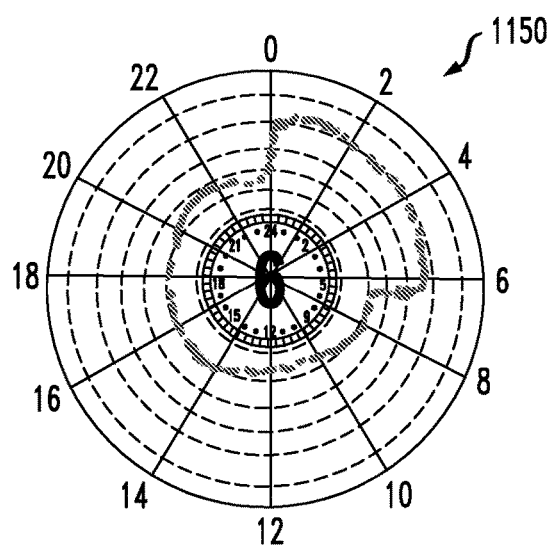

Data visualization 1150 in FIG. 11F plots a supraventricular tachycardia (SVT) physiologic metric including an accurate measure of heart rate as a monitored subject transitions into a state of SVT around midnight and recovers after wakeup at 6:00 am, illustrating cardiac conditions related to SVT.

Figure 11G:
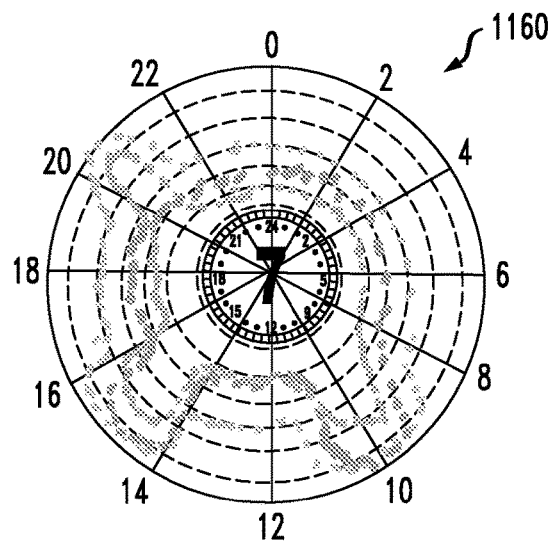

Data visualization 1160 in FIG. 11G plots heart rate, activity, and ST depression (e.g., where the trace in the ST segment of an EKG is below a baseline), illustrating a potential cardiac condition of obstructive coronary artery disease. Asymptomatic ST-segment depression with exercise can be a very strong predictor of sudden cardiac death.

Figure 11H:
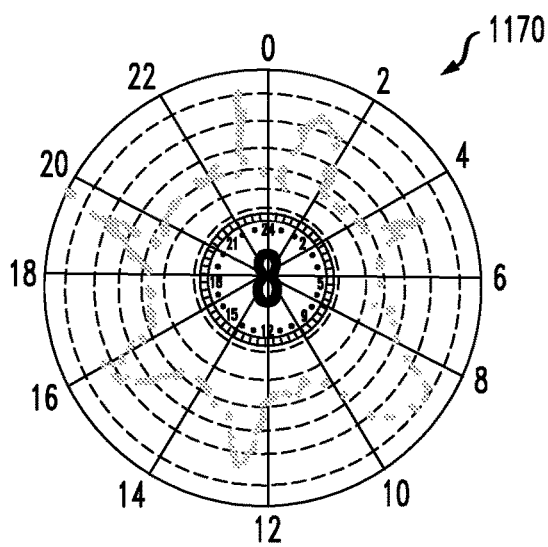

Data visualization 1170 in FIG. 11H plots RR interval physiologic metrics (e.g., a time elapsed between two successive R waves of a QRS signal on an EKG), illustrating the cardiac condition of bradycardia. Multi-parameter variants may include assessment of other metrics such as postural changes, blood pressure changes, etc. as a related event (e.g., such as a syncope event) occurs. Such information may be valuable for assessing the underlying condition a subject may be suffering from during the events.

FIGS. 12A-12D illustrate views 1200, 1210, 1220 and 1230, respectively, of the data visualization GUI 328 of data visualization system 302. In some embodiments, the data visualization GUI 328, may be implemented using a mobile computing device such as a smartphone or tablet. The mobile computing device implementing the data visualization GUI 328 may, but is not required to be, the same computing device that implements the data visualization application 320 (e.g., the data visualization system 302 may be implemented in a distributed manner, where the underlying computing resources providing or executing the data visualization application 320 or portions thereof may be distinct and possibly geographically remote from the underlying computing resources providing or executing the data visualization GUI 328). For example, at least portions of the data visualization application 320 may be implemented using a server or cloud computing platform, with only the generated data visualizations being provided to the data visualization GUI 328 running on the mobile computing device. The data visualization application 320 running on the server or cloud computing platform may, in some cases, issue prompts or requests for user selection (e.g., of data to be visualized, approval of recommended plot type choices, etc.) by displaying pop-ups or other interactive display boxes on the data visualization GUI 328 running on the mobile computing device.

Figure 12A:
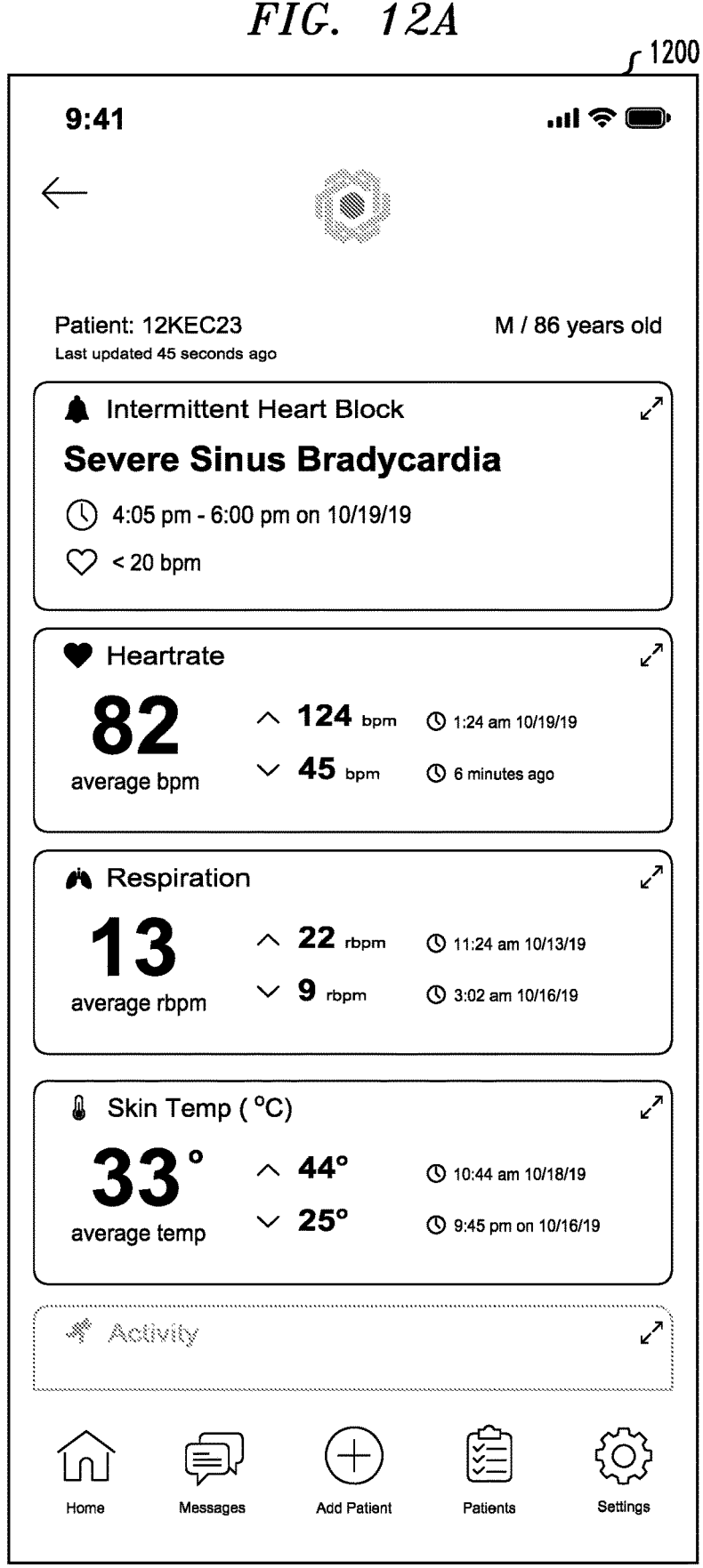
FIGS. 12A-12D illustrate additional data visualizations presented using the data visualization graphical user interface of the FIG. 3 data visualization system, according to an embodiment of the invention.
Figure 12B:
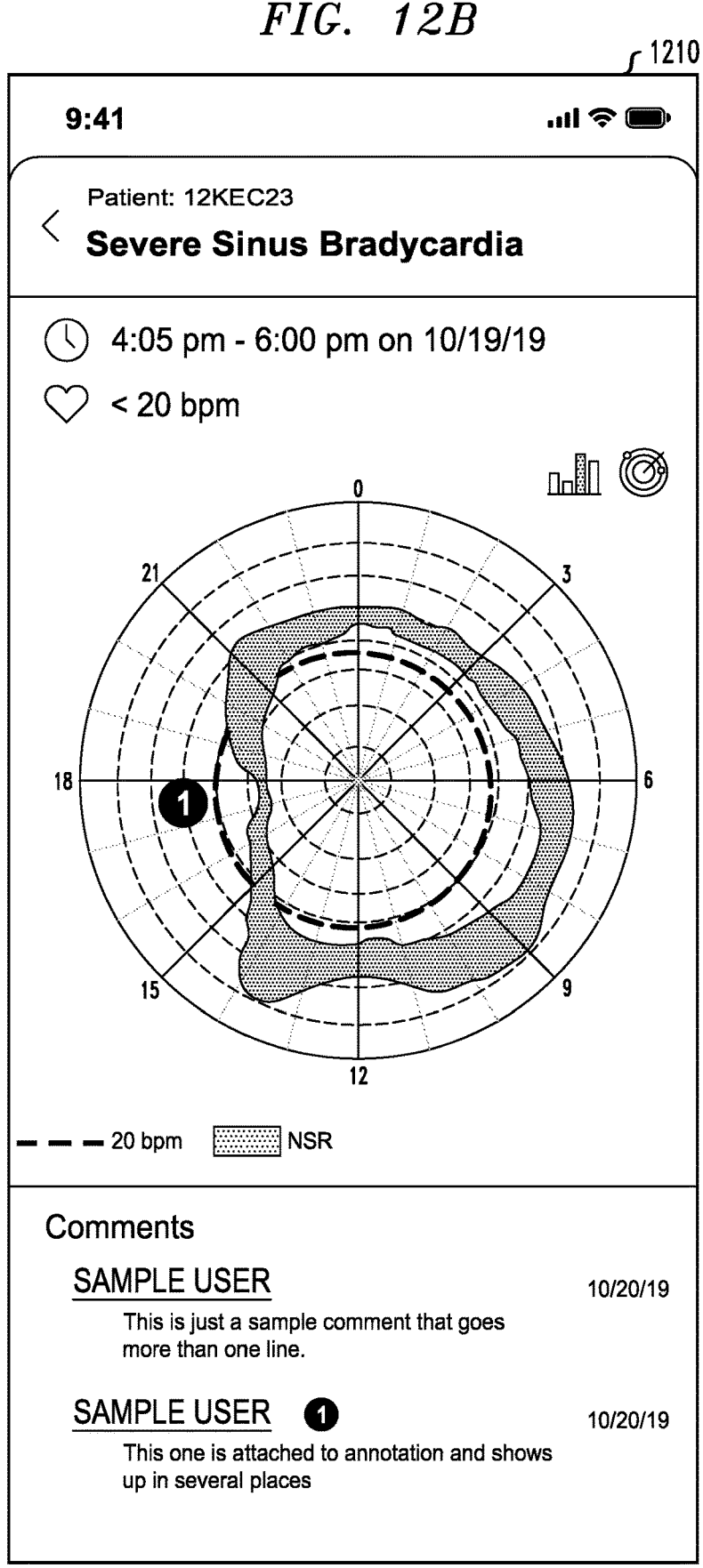
Figure 12C:
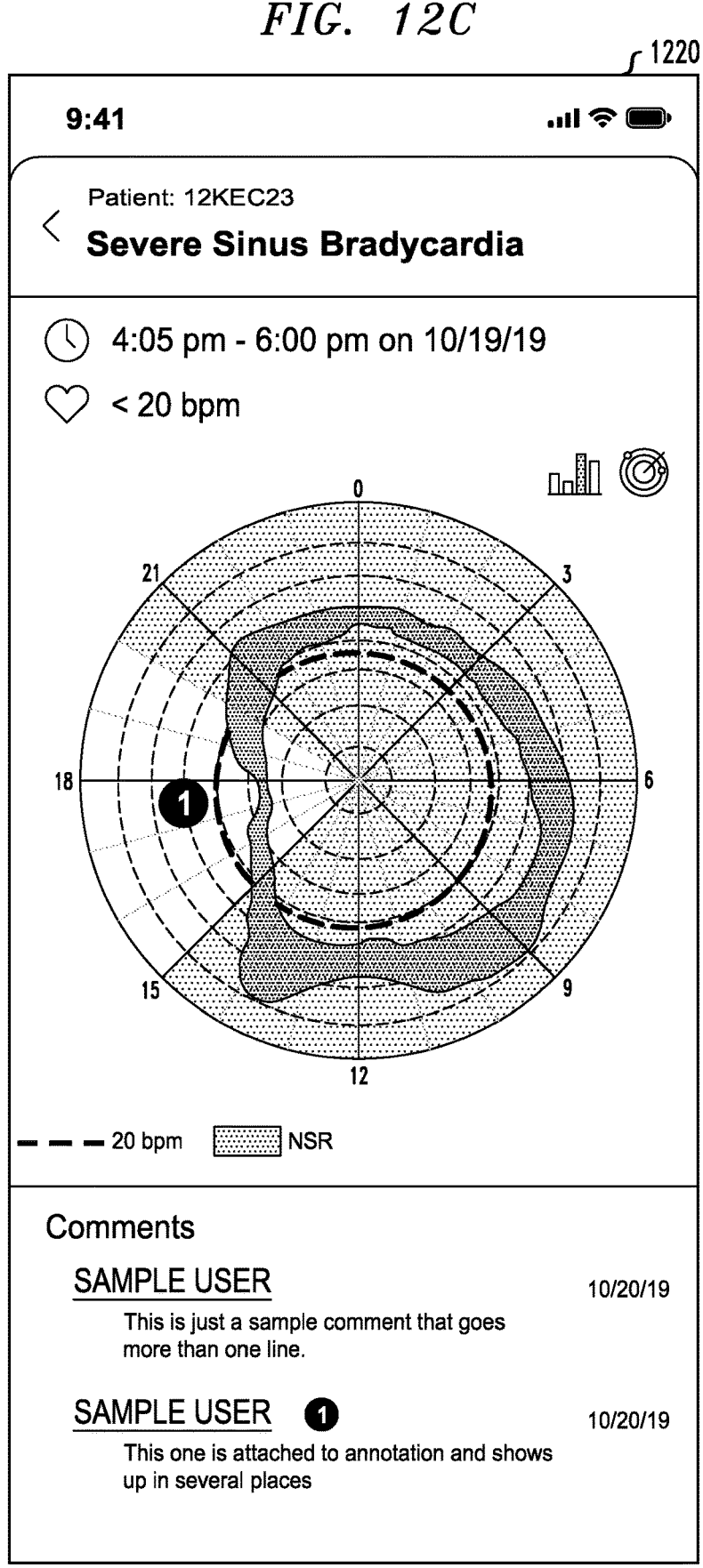
Figure 12D:
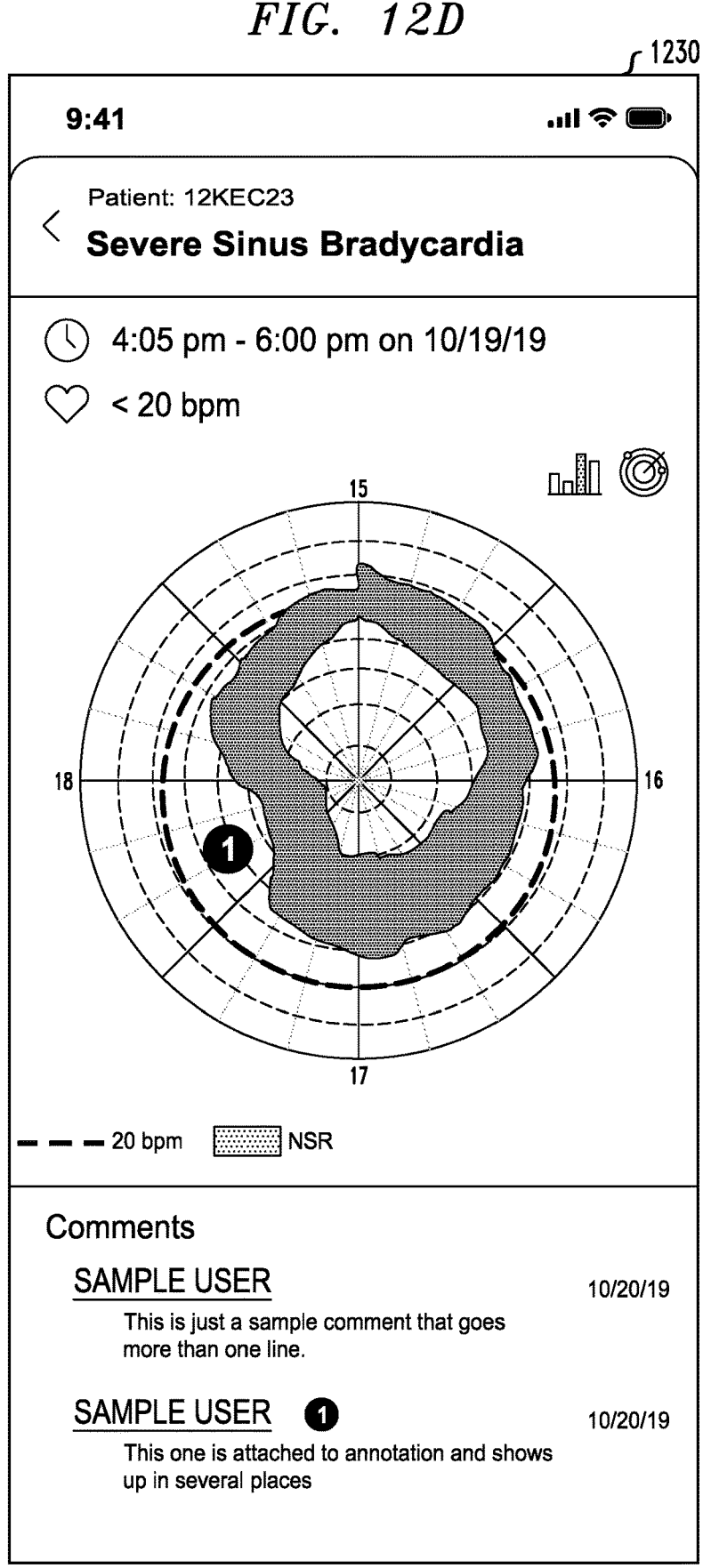

FIG. 12A shows a view 1200 of the data visualization GUI 328, showing various aspects or measured physiologic parameters for a particular patient, including an alert indicating an intermittent heart block event with severe sinus bradycardia. Responsive to user selection of the alert, the data visualization GUI 328 is updated to view 1210 of FIG. 12B, which illustrates a polar coordinate plot of heart rate corresponding to the severe sinus bradycardia event. The polar coordinate plot in view 1210 is similar to that of FIG. 10B, illustrating overlays for NSR and a heart rate of 20 bpm. The view 1210 also illustrates comments input by a sample user. One of the comments, as noted, is attached to the annotation labeled "1" in the polar coordinate plot shown. Using user interface features of the data visualization GUI 328, the user is able to "select" a portion of the polar coordinate plot as shown in view 1220 of FIG. 12C. In response to this selection, the data visualization GUI 328 zooms into the selected portion of the polar coordinate plot as illustrated in view 1230 of FIG. 12D (e.g., to examine an area of interest corresponding to the severe sinus bradycardia event).

It should be appreciated that the various physiologic metrics shown in FIGS. 11A-11H, as well as other figures such as FIGS. 9A-9B, 10A-10B and 12A-12D, are presented by way of example only. Various other types of physiologic metrics may be plotted or otherwise visualized using the techniques described herein, including any combination of desired physiologic metrics (e.g., possibly overlaid with one another and displayed for interactive user analysis in the data visualization GUI 328). The data visualization GUI 328 may also present multiple polar coordinate or other plots simultaneously on the screen if desired. FIGS. 11A-11H, as detailed above, illustrate the plotting of various physiologic metrics related to the heart and cardiac conditions, such as from an EKG.

Physiologic metrics that may be obtained from an EKG include, but are not limited to, physiologic metrics related to: heart rhythm such as ventricular ectopy (e.g., premature ventricular contractions (PVCs), coupled PVCs, ventricular tachycardia, etc.) and atrial ectopy (e.g., premature atrial contractions (PACs), atrial fibrillation, all types of SVT, etc.); heart rate (e.g., instantaneous, mean, median, etc.); QRS duration; PR interval; QT interval; RR variability, signal-averaged EKG for autonomic activity; ST segments (e.g., available at rest or exercise to correlate with activity); atrial electrogram and other options (e.g., including phonocardiogram (PCG) active and passive cycling, slow wave for ventricular motion/function); etc. Additional examples of physiologic metrics which may be plotted that are not necessarily obtained or derived from an EKG include: hemoglobin saturation; physical activity; posture; position; ST segments (e.g., utility for exercise testing review, including detecting arrhythmias); respiration (e.g., depth, rate, obstruction, etc.); activity (e.g., fitness, motion, depression/lassitude, etc.); sleep parameters (e.g., respiratory rate, respiratory depth, respiratory rhythm, obstruction, EEG, O2 saturation, position such as prone, supine, a left or right side, combinations or correlations thereof, etc.); etc.

The data visualization GUI 328, in some embodiments, enables a daily "infinitely" navigable display, with various options for plots displayed thereon. Such options include color (e.g., selectable by a user to represent various status, to highlight particular variable or physiologic parameters, etc.), amplitude, shading or gradient, density, etc. The data visualization GUI 328 may include a screen layout that allows for one or multiple plots to be displayed. For example, one or more polar coordinate plots may be displayed. Such polar coordinate plots may be created at will (e.g., utilizing the data visualization application 320 as detailed above), with no limit on the number of plots created. The polar coordinate plots may be used to display any single variable or physiologic parameter, or any desired combination of variables or physiologic parameters. Individual polar coordinate plots or groups of the polar coordinate plots may be opened, closed, put to sleep, etc. Individual polar coordinate plots or groups of the polar coordinate plots may also be drag-and-dropped to desired areas of a screen, and may be resized as desired. In some embodiments, multiple polar coordinate plots are arranged as an ensemble as selected by a user (e.g., using 7 polar plot displays, one for each day of the week). The data visualization GUI 328 enables a user to click or select anywhere in the display.

Figure 13A:
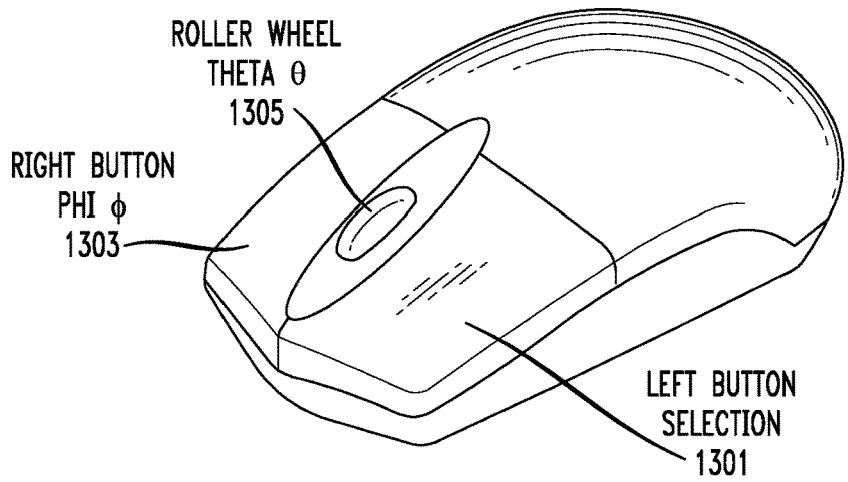
FIGS. 13A-13C illustrate user interface features of a data visualization graphical user interface, according to an embodiment of the invention.
Figure 13B:
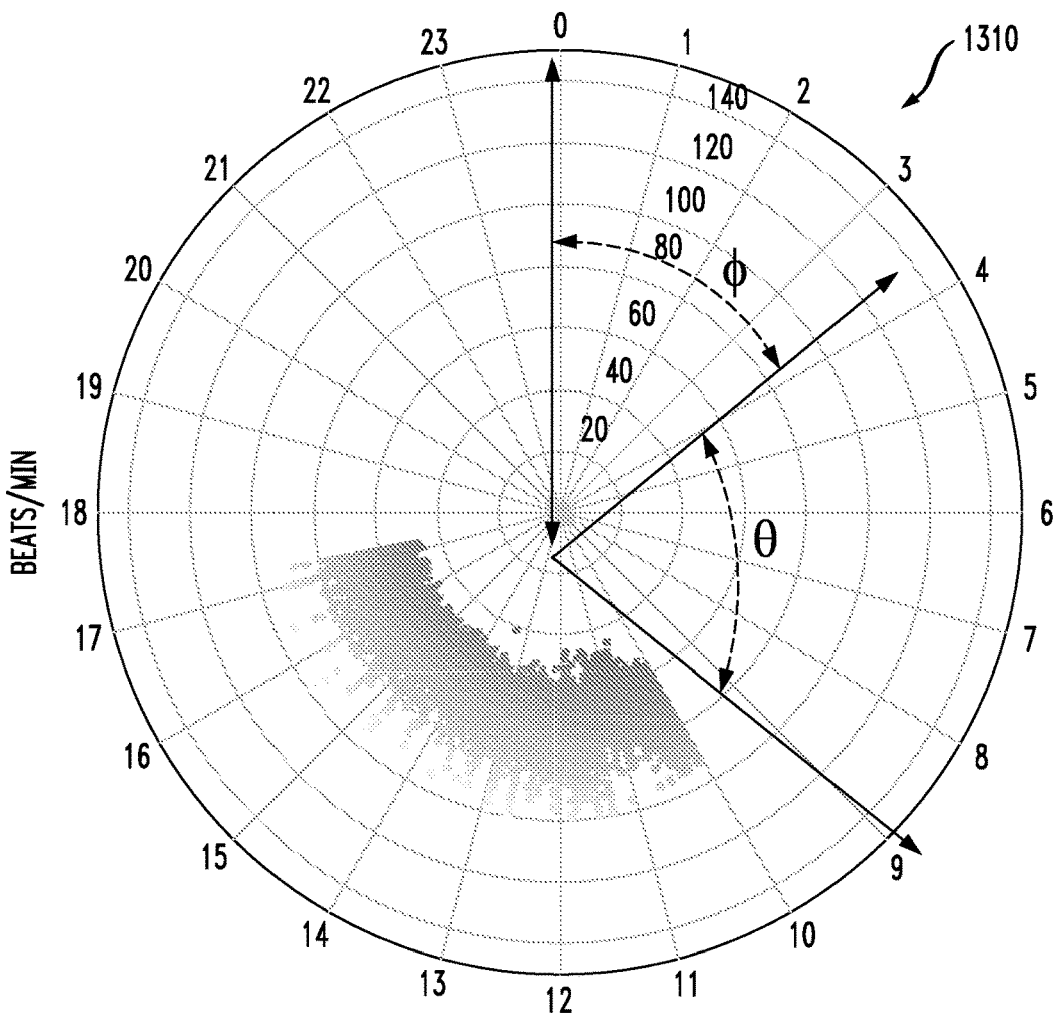

The data visualization GUI 328 allows a user to "click" anywhere in a display (e.g., where the click may be using one or more mouse buttons, regions of a touch interface, keys on a keyboard, other input devices, etc.). FIG. 13A shows a view of a mouse, illustrating how the left button 1301 may be used to select, while the right button 1303 controls phi Φ as shown in view 1310 of FIG. 13B, and the mouse wheel 1305 controls theta θ as shown in view 1310 of FIG. 13B. The mouse wheel 1305 yields a "wedge" (e.g., as shown in view 1220 of FIG. 12C described above) that opens and closes to set the size the user wishes to display. The selected data may be automatically inserted into a data window (e.g., such as updating the polar coordinate plot as shown in view 1230 of FIG. 12D described above). In some embodiments, clicking using the roller wheel 1305 may open another "nearby" polar coordinate plot display whose arc limits are those determined by the wedge arclength. The "nearby" location is such that it is clear that the new polar coordinate plot display is that of the original polar coordinate plot display or an associated linear box signal display. Alternatively, the user can drag anywhere on the radial ray to move it around the circle. As dragged, the display in the data boxes is updated and the mouse wheel 1305 remains active for wedge selection. Alternatively, the user may "hold down and roll" to change the shape and size of the wedge with the mouse wheel 1305.

The data visualization GUI 328, in some embodiments, includes a series of raw data box displays. A user may "click and drag" from a polar coordinate plot display into a data box, or may alternatively click on a data box to make that data "live" in a polar coordinate plot display. Clicking anywhere in a polar coordinate plot display may give default data of a certain specified or default (which may be user defined) arc or linear length. One or both vectors may be labeled for radial distance scale (e.g., larger radii for higher heart rate). This permits instant visualization of high and low magnitudes. The scale vector may be independently moveable (e.g., grab the tip with the mouse and move around the circumference to the desired measurement location). The data visualization GUI 328 also enables simultaneous display of multiple data variables or physiologic parameters in a single data box or polar coordinate plot (or other plot type), such as using overlays and overlaps, for direct top-bottom comparison, etc.

As noted above, in some embodiments a mouse may be used as an input device for interacting with the data visualization GUI 328. The left button 1301 of the mouse shown in FIG. 13A may be used to "click" anywhere on a polar coordinate plot (or other type of visualization). The left button 1301, in some embodiments, may be double-clicked to expand a wedge into a full circle, or to do automatic rescaling of a desired time interval. The mouse wheel 1305 may be used for zooming in and out. The right button 1303 may be used for Azimuth rotation of the wedge, making it easy to review other information in a polar coordinate plot.

As described above, the data visualization GUI 328 enables opening of new and multiple windows or data visualizations with different plots (e.g., polar coordinate plots, Cartesian coordinate plots, etc.). This may be useful in various multi-time applications, such as treadmill exercise using a multi-12 lead EKG summary for plotting: ST elevation and depression; heart rate and associated conditions such as tachycardia, bradycardia, regularity and irregularity, pauses, etc., where desired conditions may be selectively emphasized using designated colors, sizes, etc.; QT intervals; etc. Such various plots may be used to observe progression throughout a test on a single or simple polar coordinate plot or map of such plots. Further, various contextual overlays may be plotted or used to filter or annotate the plots. Contextual data may be obtained from various devices associated with a subject, such as smart home devices, Internet of Things (IoT) devices, smart televisions, computers, phones, automobiles, location services, global positioning services (GPS), etc.

Figure 13C:
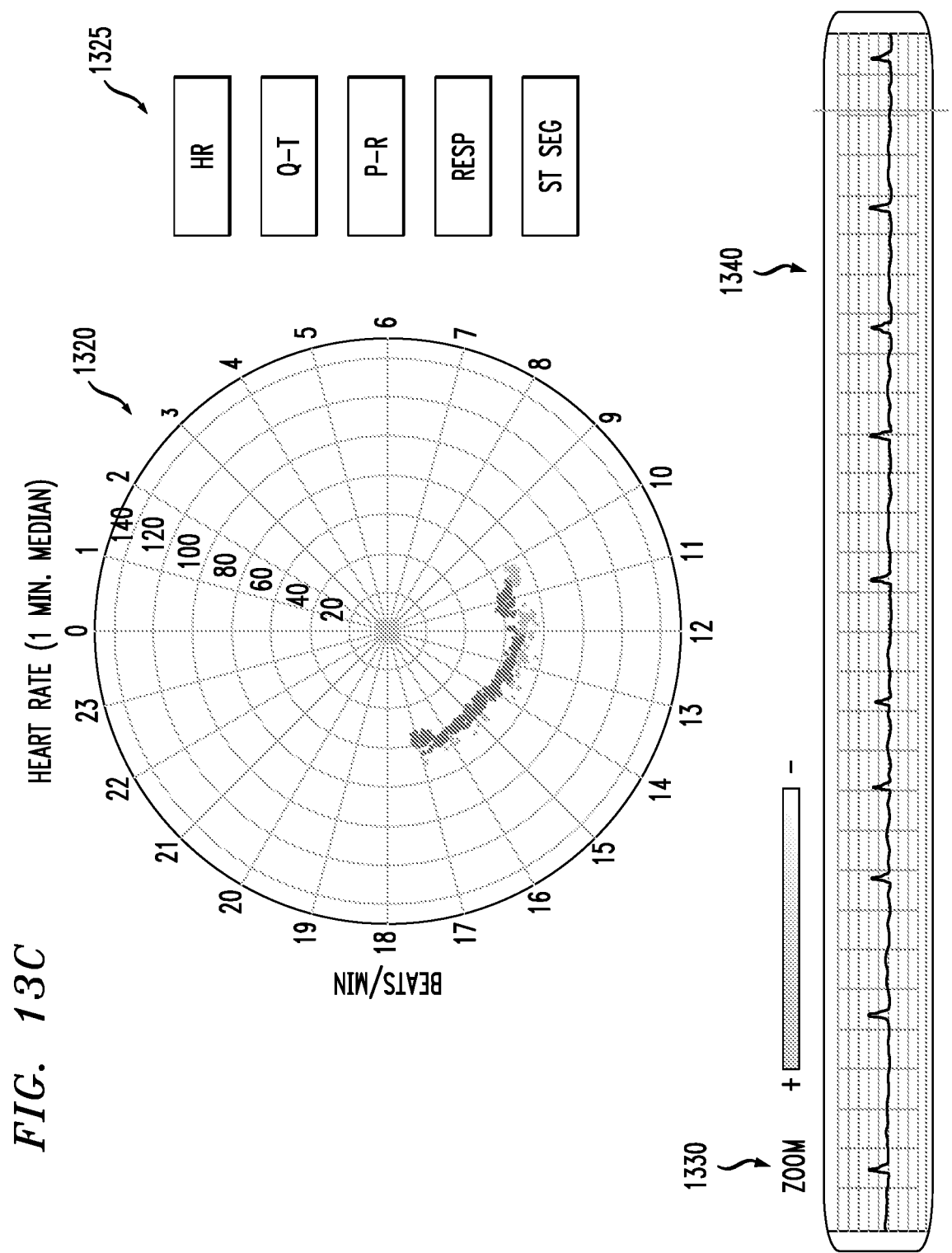

Data boxes, as noted above, may be used to show the raw data at any point or region as selected on a polar coordinate plot or other data visualization. FIG. 13C, for example, shows a polar coordinate plot visualization 1320 of heart rate (e.g., a one minute median), a set of physiologic parameters 1325 which may be selected to overlay on the polar coordinate plot 1320, a user interface feature 1330 for zooming in and out on portions of the polar coordinate plot 1320, and a linear trace 1340 of the data in the polar coordinate plot.

Polar coordinate plots may be created at will in the data visualization GUI 328, in any number. A newly created polar coordinate plot may be displayed "nearby" to the associated data box, with an option to open or close connected polar coordinate plot displays. Multiple data sets may be displayed as desired for direct overlap or comparison. The polar coordinate plots may be opened or closed and resized similar to other graphics. The data visualization GUI 328 may also include analytic boxes created to show direct analysis of data including statistics. The analytic boxes may also be used for correlation amongst variables. Correlation analysis (e.g., linear, exponential, polynomial, etc.) may be drawn as desired at user discretion. The analytics boxes may also yield and display correlation statistics and equations as desired, including but not limited to correlation and other statistical analysis such as: mean, mode or other descriptive statistics; frequencies of occurrence; bar charts, or any other graphic display; frequency histograms; simple zoom in or out via the mouse wheel 1305 or dragging with other buttons; etc.

The data visualization GUI 328 also enables various notation features. Notations may be displayed on any data (e.g., of a plot such as a polar coordinate plot). As one example, an annotation may be displayed on a circumference of a polar coordinate plot corresponding to a particular time. Notations may be obtained from various sources (e.g., from sensing devices associated with a subject, from one or more patch/module pairs as described herein, etc.). Consider, as an example, a patch/module pair that allows a user to initiate voice recordings. The user may do so when experiencing various symptoms (e.g., discomfort, pain, etc.) or when performing various activities (e.g., taking a medication, changing posture or position, etc.). Such voice recordings may annotate a plot of physiologic metric data that is obtained at or near the time that the voice recording is initiated. In some embodiments, the voice recording itself is annotated (e.g., as a playable media element) or may be transcribed into text, where the voice recording or transcribed text may be listened to or viewed by opening or clicking on a "bubble" or other interface feature on the circumference of a polar coordinate plot. An example annotation "1" is shown and described above in conjunction with FIGS. 12B-12D. Annotations may be taken directly from a subject or another individual (e.g., a caregiver, nurse, doctor, etc.) and may be written, typed, spoken, or otherwise input. The annotations may appear as a voice box or icon at the arc time point indicated by an internal clock (e.g., as text using voice-to-text or spoken-to-voice recognition, as direct voice playback of the patient through a speaker module on a device implementing the data visualization GUI 328, etc.). Annotations may be used for correlation of measured physiologic parameters (e.g., of an EKG) with symptoms or other patient information inserted by a patient or caregiver associated with the patient.

The data visualization GUI 328 enables various data selection and data visualization customizations by interacting or selecting different parts of a screen (e.g., using left button 1301 of a mouse or other suitable input feature of an input device). Such customizations include, but are not limited to colors, toggling aspects of a display on or off, setting (e.g., including enabling or disabling) various thresholds (e.g., maximums and minimums, different colors or shadings for different levels such as the different colors or shadings used for different bpm ranges in visualizations 900 and 910 of FIGS. 9A and 9B described above). The data visualization GUI 328 also provides features enabling a user to save particular data visualizations (e.g., polar coordinate plots) to local or remote (e.g., cloud) storage.

The data visualization GUI 328 is configured to accept real-time data from anywhere in various display sections. Date and time may be set manually (e.g., to look at specific events). The data visualization GUI 328 may also enable sound (e.g., to play voice recording annotations). User interface features may also be provided in the data visualization GUI 328 for setting the start and end of a circle of a polar coordinate plot (e.g., including using defaults with possible manual overrides), for zooming in and out of waveforms (e.g., using element 1330 in FIG. 13C) including by clicking or holding and dragging, for toggling display of various variables and physiologic parameters (e.g., toggling PCG, T wave and other signal processing available from EKG tracings), using multiple polar coordinate plots or other data visualizations for comparing with previous data (e.g., previous EKG tracings). The data visualization GUI 328 may be used to reconstruct a 12-lead EKG from selected EKG rhythm waveforms, using data boxes or other interface features for a 12-lead EKG in addition to polar coordinate plots for rhythms or for comparing to prior tracings, etc. The data visualization GUI 328 in some embodiments may allow toggling a small calendar on and off for selecting data to be displayed, for saving and sending selected data visualizations (e.g., to other devices implementing instances of the data visualization GUI 328, such as for sharing between multiple caregivers associated with a patient, etc.). The data visualization GUI 328, in addition to displaying annotations provided by a patient or associated caregiver, may also enable the user of the data visualization GUI 328 to add annotations to data visualizations and/or the underlying data.

An exemplary process 1400 for visualizing physiologic data obtained from subjects will now be described with reference to the flow diagram of FIG. 14. It should be understood, however, that this particular process is only an example and that other types of processes for visualizing physiologic data obtained from subjects may be used in other embodiments as described elsewhere herein. The process 1400 includes steps 1402 through 1408, and is assumed to be performing by the data visualization system 302 (e.g., utilizing data visualization application 320, data selection module 322, data visualization recommendation module 324, data visualization generation module 326 and data visualization GUI 328.

The process 1400 begins with step 1402, selecting physiologic data to be visualized. The selected physiologic data comprises a given set of one or more physiologic parameters collected from a given set of one or more subjects over a given period of time. Step 1402 may include selecting the given set of one or more subjects, the given set of one or more physiologic parameters, and the given period of time from a database of available physiologic data (e.g., physiologic data database 308). The database of available physiologic data may comprise a plurality of entries, each entry being associated with a given subject identifier for a given one of a plurality of subjects, a given timestamp, and a plurality of physiologic parameters collected from the given subject at the given timestamp. Selecting the physiologic data to be visualized from the database of available physiologic data may comprise obtaining the given set of one or more physiologic parameters from a selected subset of entries from the database of available physiologic data, the selected subset of entries having subject identifiers for the given set of one or more subjects and timestamps within the given period of time.

In step 1404, a plot type for visualization of the selected physiologic data is determined. The plot type is determined based at least in part on a repetitiveness of the selected physiologic data over a plurality of time segments in the given period of time. A visualization of the selected physiologic data is generated in step 1406 utilizing the determined plot type. The generated visualization of the selected physiologic data is output in step 1408 via an interactive GUI (e.g., data visualization GUI 328).

Step 1404 may include dividing the given period of time into the plurality of time segments, comparing data in at least a subset of a plurality of possible pairs of the plurality of time segments for repetitiveness, and, responsive to determining that the data in at least a threshold number of the plurality of possible pairs of the plurality of time segments are repetitive with respect to one another, selecting a polar coordinate plot type for visualizing the selected physiologic data. Responsive to determining that the data in at least the threshold number of the plurality of possible pairs of the plurality of time segments are not repetitive with respect to one another, a Cartesian coordinate plot type may be selected for visualizing the selected physiologic data. The threshold number of the plurality of possible pairs of the plurality of time segments may comprise a designated percentage of a total number of the plurality of possible pairs of the plurality of time segments.

In some embodiments, step 1404 includes identifying a set of supported time segment sizes, and performing one or more iterations of (i) dividing the given period of time into the plurality of time segments utilizing a given one of the set of supported time segment sizes and (ii) comparing the data in at least the subset of the plurality of possible pairs of the plurality of time segments of the given supported time segment size, until a determination is made that the data in at least the threshold number of the plurality of possible pairs of the plurality of time segments of the given supported time segment size are repetitive with respect to one another. A first one of the one or more iterations may utilize a smallest one of the set of supported time segment sizes and one or more subsequent ones of the one or more iterations may utilize next largest ones of the set of supported time segment sizes. The smallest one of the set of supported time segment sizes, in some embodiments, is one day. Responsive to determining that the data in at least the threshold number of the plurality of possible pairs of the plurality of time segments are not repetitive with respect to one another in at least a threshold number of the one or more iterations, step 1404 may include selecting a Cartesian coordinate plot type for visualizing the selected physiologic data.

In some embodiments, step 1402 includes identifying one or more annotations associated with one or more designated time ranges within the given period of time, and step 1408 includes displaying one or more user-activatable interface features for the one or more annotations at respective points along a circumference of the polar coordinate plot corresponding to the one or more designated time ranges within the given period of time. At least a given one of the one or more annotations may comprise one or more contextual events associated with the given subject at a given one of the one or more designated time ranges. At least a given one of the one or more contextual events comprises at least one of: administering a medication to the given subject; a change in posture or position of the given subject; an indication of pain or discomfort of the given subject; an indication of a sleep state of the given subject; and an indication of a physical activity level of the given subject. The given annotation in some embodiments comprises a voice recording captured by a given one of the subjects or a caregiver of the given subject, the voice recording describing at least a given one of the one or more contextual events.

Step 1408 may include providing one or more user-activatable interface features for overlaying one or more filters on the polar coordinate plot. Each of the plurality of time segments may comprise one day, and at least a given one of the one or more filters may comprise overlaying visual indicators of daytime and nighttime on the polar coordinate plot, overlaying visual indicators of a sleep state of a given one of the one or more subjects on the polar coordinate plot, etc. At least a given one of the one or more filters may comprise displaying a threshold value of a given one of the one or more physiologic parameters as a ring on the polar coordinate plot.

In some embodiments, step 1408 includes providing one or more user-activatable interface features for toggling display of individual ones of the set of one or more physiologic parameters on the polar coordinate plot, for selecting a given region of the polar coordinate plot corresponding to a given time range within the given period of time, etc. Responsive to selecting the given region of the polar coordinate plot, the interactive GUI may update the polar coordinate plot to zoom in to the given time range corresponding to the selected given region of the polar coordinate plot, present an additional polar coordinate plot that is zoomed in to the given time range corresponding to the selected given region of the polar coordinate plot, etc. Step 1408 may also include outputting a linear time trace of at least a given one of the set of one or more physiologic parameters, and wherein responsive to selecting the given region of the given polar coordinate plot the interactive GUI zooms the linear time trace to the given time range corresponding to the selected given region of the polar coordinate plot.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:
1. An apparatus comprising:
   at least one processing device comprising a processor coupled to a memory;
   the at least one processing device being configured:
   to select physiologic data to be visualized, the selected physiologic data comprising a given set of one or more physiologic parameters collected from a given set of one or more subjects over a given period of time;
   to determine a plot type for visualization of the selected physiologic data, the plot type being determined based at least in part on a repetitiveness of the selected physiologic data over a plurality of time segments in the given period of time;

to generate a visualization of the selected physiologic data utilizing the determined plot type; and to output the generated visualization of the selected physiologic data via an interactive graphical user interface;

wherein determining the plot type for the visualization comprises (i) selecting a polar coordinate plot type responsive to determining that the selected physiologic data has at least a threshold level of repetitiveness over the plurality of time segments in the given period of time and (ii) selecting a Cartesian coordinate plot type responsive to determining that the selected physiologic data does not have at least the threshold level of repetitiveness over the plurality of time segments in the given period of time.

2. The apparatus of claim 1, wherein:

selecting the physiologic data to be visualized comprises selecting the given set of one or more subjects, the given set of one or more physiologic parameters, and the given period of time from a database of available physiologic data;

the database of available physiologic data comprises a plurality of entries, each entry being associated with a given subject identifier for a given one of a plurality of subjects, a given timestamp, and a plurality of physiologic parameters collected from the given subject at the given timestamp; and selecting the physiologic data to be visualized from the database of available physiologic data comprises obtaining the given set of one or more physiologic parameters from a selected subset of entries from the database of available physiologic data, the selected subset of entries having subject identifiers for the given set of one or more subjects and timestamps within the given period of time.

3. The apparatus of claim 1, wherein determining the plot type for visualization of the selected physiologic data comprises:

dividing the given period of time into the plurality of time segments;

comparing data in at least a subset of a plurality of possible pairs of the plurality of time segments for repetitiveness; and responsive to determining that the data in at least a threshold number of the plurality of possible pairs of the plurality of time segments are repetitive with respect to one another, selecting the polar coordinate plot type for visualizing the selected physiologic data.

4. The apparatus of claim 3 wherein, responsive to determining that the data in at least the threshold number of the plurality of possible pairs of the plurality of time segments are not repetitive with respect to one another, selecting the Cartesian coordinate plot type for visualizing the selected physiologic data.

5. The apparatus of claim 3, wherein determining the plot type for visualization of the selected physiologic data further comprises identifying a set of supported time segment sizes, and performing one or more iterations of (i) dividing the given period of time into the plurality of time segments utilizing a given one of the set of supported time segment sizes and (ii) comparing the data in at least the subset of the plurality of possible pairs of the plurality of time segments of the given supported time segment size, until a determination is made as to whether the data in at least the threshold number of the plurality of possible pairs of the plurality of time segments of the given supported time segment size are repetitive with respect to one another.

6. The apparatus of claim 5, wherein a first one of the one or more iterations utilizes a smallest one of the set of supported time segment sizes and one or more subsequent ones of the one or more iterations utilize next largest ones of the set of supported time segment sizes.

7. The apparatus of claim 5, wherein responsive to determining that the data in at least the threshold number of the plurality of possible pairs of the plurality of time segments are not repetitive with respect to one another in at least a threshold number of the one or more iterations, selecting the Cartesian coordinate plot type for visualizing the selected physiologic data.

8. The apparatus of claim 3, wherein selecting the physiologic data to be visualized further comprises identifying one or more annotations associated with one or more designated time ranges within the given period of time, and wherein outputting the generated visualization of the selected physiologic data via the interactive graphical user interface comprises displaying one or more user-activable interface features for the one or more annotations at respective points along a circumference of a polar coordinate plot corresponding to the one or more designated time ranges within the given period of time.

9. The apparatus of claim 8, wherein at least a given one of the one or more annotations comprises one or more contextual events associated with the given subject at a given one of the one or more designated time ranges, wherein at least a given one of the one or more contextual events comprises at least one of:

administering a medication to the given subject;
a change in posture or position of the given subject;
an indication of pain or discomfort of the given subject;
an indication of a sleep state of the given subject; and
an indication of a physical activity level of the given subject.

10. The apparatus of claim 9, wherein the given annotation comprises a voice recording captured by a given one of the subjects or a caregiver of the given subject, the voice recording describing at least a given one of the one or more contextual events.

11. The apparatus of claim 3, wherein outputting the generated visualization of the selected physiologic data via the interactive graphical user interface comprises providing one or more user-activatable interface features for overlaying one or more filters on a polar coordinate plot.

12. The apparatus of claim 11, wherein each of the plurality of time segments comprises one day, and wherein at least a given one of the one or more filters comprises overlaying visual indicators of daytime and nighttime on the polar coordinate plot.

13. The apparatus of claim 11, wherein each of the plurality of time segments comprises one day, and wherein at least a given one of the one or more filters comprises overlaying visual indicators of a sleep state of a given one of the one or more subjects on the polar coordinate plot.

14. The apparatus of claim 11, wherein at least a given one of the one or more filters comprises displaying a threshold value of a given one of the one or more physiologic parameters as a ring on the polar coordinate plot.

15. The apparatus of claim 3, wherein outputting the generated visualization of the selected physiologic data via the interactive graphical user interface comprises providing one or more user-activatable interface features for toggling display of individual ones of the set of one or more physiologic parameters on a polar coordinate plot.

16. The apparatus of claim 3, wherein outputting the generated visualization of the selected physiologic data via the interactive graphical user interface comprises providing one or more user-activatable interface features for selecting a given region of a polar coordinate plot corresponding to a given time range within the given period of time.

17. The apparatus of claim 16, wherein responsive to selecting the given region of the polar coordinate plot, the interactive graphical user interface one of:
   updates the polar coordinate plot to zoom in to the given time range corresponding to the selected given region of the polar coordinate plot; and
   presents an additional polar coordinate plot that is zoomed in to the given time range corresponding to the selected given region of the polar coordinate plot.

18. The apparatus of claim 16, wherein outputting the generated visualization of the selected physiologic data further comprises outputting a linear time trace of at least a given one of the set of one or more physiologic parameters, and wherein responsive to selecting the given region of the given polar coordinate plot the interactive graphical user interface zooms the linear time trace to the given time range corresponding to the selected given region of the polar coordinate plot.

19. A computer program product comprising a non-transitory processor-readable storage medium having stored therein executable program code which, when executed, causes at least one processing device:
   to select physiologic data to be visualized, the selected physiologic data comprising a given set of one or more physiologic parameters collected from a given set of one or more subjects over a given period of time;
   to determine a plot type for visualization of the selected physiologic data, the plot type being determined based at least in part on a repetitiveness of the selected physiologic data over a plurality of time segments in the given period of time;
   to generate a visualization of the selected physiologic data utilizing the determined plot type; and
   to output the generated visualization of the selected physiologic data via an interactive graphical user interface;
   wherein determining the plot type for the visualization comprises (i) selecting a polar coordinate plot type responsive to determining that the selected physiologic data has at least a threshold level of repetitiveness over the plurality of time segments in the given period of time and (ii) selecting a Cartesian coordinate plot type responsive to determining that the selected physiologic data does not have at least the threshold level of repetitiveness over the plurality of time segments in the given period of time.

20. A method comprising:
   selecting physiologic data to be visualized, the selected physiologic data comprising a given set of one or more physiologic parameters collected from a given set of one or more subjects over a given period of time;
   determining a plot type for visualization of the selected physiologic data, the plot type being determined based at least in part on a repetitiveness of the selected physiologic data over a plurality of time segments in the given period of time;
   generating a visualization of the selected physiologic data utilizing the determined plot type; and
   outputting the generated visualization of the selected physiologic data via an interactive graphical user interface;
   wherein determining the plot type for the visualization comprises (i) selecting a polar coordinate plot type responsive to determining that the selected physiologic data has at least a threshold level of repetitiveness over the plurality of time segments in the given period of time and (ii) selecting a Cartesian coordinate plot type responsive to determining that the selected physiologic data does not have at least the threshold level of repetitiveness over the plurality of time segments in the given period of time; and
   wherein the method is performed by at least one processing device comprising a processor coupled to a memory.

\* \* \* \* \*